United States Patent
Redfield et al.

(10) Patent No.: US 6,479,466 B1
(45) Date of Patent: Nov. 12, 2002

(54) COMPOSITIONS FOR TREATING VIRAL INFECTIONS, AND METHODS THEREFOR

(75) Inventors: Robert R. Redfield, Baltimore, MD (US); Charles E. Davis, Jr., Laurel, MD (US); Alonso Heredia, Washington, DC (US)

(73) Assignees: University of Maryland, Baltimore, MD (US); University of Maryland Biotechnology Institute, Baltimore, MD (US)

( * ) Notice: Subject to any disclaimer, the term of this patent is extended or adjusted under 35 U.S.C. 154(b) by 198 days.

(21) Appl. No.: 09/637,652

(22) Filed: Aug. 11, 2000

Related U.S. Application Data
(60) Provisional application No. 60/149,029, filed on Aug. 13, 1999.

(51) Int. Cl.$^7$ .................... A61K 31/52; A61K 31/505; A61K 31/552; A61K 31/70
(52) U.S. Cl. ................ 514/45; 514/46; 514/49; 514/50; 514/263.23; 514/263.32; 514/263.4; 514/272
(58) Field of Search ................ 514/263.23, 263.37, 514/263.4, 272, 45, 46, 49, 50

(56) References Cited

U.S. PATENT DOCUMENTS

| | | | |
|---|---|---|---|
| 5,026,687 A | 6/1991 | Yarchoan et al. | 514/45 |
| 5,178,865 A | 1/1993 | Ho et al. | 424/195.1 |
| 5,521,161 A | 5/1996 | Malley et al. | 514/45 |
| 5,736,526 A | 4/1998 | Malley et al. | 514/45 |
| 5,736,527 A | 4/1998 | Malley et al. | 514/45 |
| 5,747,536 A | 5/1998 | Cavazza | 514/556 |
| 5,834,268 A | 11/1998 | Hain et al. | 435/172.3 |
| 5,837,257 A | 11/1998 | Tsai et al. | 424/195.1 |
| 6,008,260 A | 12/1999 | Pezzuto et al. | 514/733 |
| 6,043,250 A * | 3/2000 | Klein et al. | 514/263 |

FOREIGN PATENT DOCUMENTS

| | | |
|---|---|---|
| WO | WO89/02733 | 4/1989 |
| WO | WO99/03816 | 1/1999 |
| WO | WO99/58119 | 11/1999 |
| WO | WO01/12228 | 2/2001 |

OTHER PUBLICATIONS

Bianchi et al., "Inhibition of ribonucleotide reductase by 2'–substituted deoxycytidine analogs: possible application in AIDS treatment," *Proc. Natl. Acad. Sci. USA*, 91:8403–8407, Aug. 1994.

Davis et al., "The synergistic inhibition of HIV–1 in activated and resting peripheral blood mononuclear cells, monocyte–derived macrophages, and selected drug–resistant isolated with nucleoside analogs combined with a natural product, resveratrol," *Institute of Human Virology, University of Maryland Biotechnology Institute and University of Maryland Medicine; Department of Medicine, and Department of Microbiology and Immunology*, Apr., 2000.

Docherty et al., "Resveratrol inhibition of herpes simplex virus replication," *Antiviral Research*, 43(3):135–145, Oct. 1999.

Elford, "Effect of Hydroxyurea on ribonucleotide reductase," *Biochemical and Biophysical Research Communications*, 33(1):129–135, 1968.

Fontecave et al., "Resveratrol, a remarkable inhibitor of ribonucleotide reductase," *FEBS Letters*, 421:227–279, Jan. 2, 1998.

Gao et al., "Disparate actions of hydroxyurea in potentiation of purine and pyrimidine 2',3'–dideoxynucleoside activities against replication of human immunodeficiency virus," *Proc. Natl. Acad. Sci. USA*, 92:8333–8337, Aug. 1995.

Heredia et al., "In vitro synergistic antiretroviral activities of abacavir/mycophenolic acid and DDI/resveratrol combinations against multi–drug resistant HIV–1 (RT Mutants) suggest a new approach to control resistance," *Keystone Conference.*, Apr., 2000.

Hsieh et al., "Resveratrol increases nitric oxide synthase, induces accumlation of p53 and p21$^{WAF1/CIP1}$, and suppresses cultured bovine pulmonary artery endothelial cell proliferation by perturbing progression through S and G$_2$ $^1$," *Cancer Research*, 59:2596–2601, Jun. 1, 1999.

Krakoff et al., "Inhibition of ribonucleoside diphosphate reductase by hydroxyurea," *Cancer Research*, 28:1559–1565, Aug. 1968.

Lori et al., "Long–term suppression of HIV–1 by hydroxyurea and didanosine," *JAMA*, 277(18):1437–1438, May 14, 1997.

Lori et al., "Combination of a drug targeting the cell with a drug targeting the virus controls human immunodeficiency virus type 1 resistance," *AIDS Research and Human Retroviruses*, 13(16):1403–1409, 1997.

Lori et al., "Hydroxyurea as an inhibitor of human immunodeficiency virus–type 1 replication," *Science*, 266:801–805, Nov. 4, 1994.

Ragione et al., "Resveratrol arrests the cell division cycle at S/G2 phase transition," *Biochemical and Biophysical Research Communications*, 250:53–58, Sep. 1998.

Reichard, "Interactions bewteen deoxyribonucleotide and DNA synthesis," *Ann. Rev. Biochem.*, 57:349–74, 1988.

"Resveratrol Sigma Prod. No. R5010," *Sigma Chemical Company* Product Information, Jul. 11, 1997.

Soleas et al., "Resveratrol: a molecule whose time has come? and gone?," *Clinical Biochemistry*, 30(2):91–113, 1997.

(List continued on next page.)

Primary Examiner—Peter O'Sullivan
(74) Attorney, Agent, or Firm—Steven J. Hultquist; Marianne Fuierer; Yongzhi Yang

(57) ABSTRACT

Methods and combinations of an agent that promotes DNA synthesis in a virally-targeted cell and a nucleoside analogue having antiviral activity are provided for treating a viral infection in a subject in need thereof. Such compositions are particularly effective where the subject has resistance to a nucleoside analogue, where the subject has resting cellular reservoirs of such a virus, or to induce a post-treatment period of replication incompetence of such a virus.

31 Claims, 11 Drawing Sheets

OTHER PUBLICATIONS

Thakkar et al., "Synthesis and protein–tyrosine kinase inhibitory activity of polyhydroxylated stilbene analogues of piceatannol," *J. Med. Chem.*, 36:2950–2955, 1993.

Young et al., "Inhibition of DNA synthesis by hydroxyurea: structure–activity relationships," *Cancer Research*, 27(1):535–540, Mar. 1967.

Galpin, J.E. et al., "Safety, Sheltering, & Synergy of Hydroxyurea (HU with ddI or ddI Plus d4T In HIV–infected Patients", *5th Conference on Retroviruses and Opportunistic Infections*, Chicago, IL; Feb. 1–5, 1998.

Little, S., et al., "The Spectrum and Frequency of Reduced Antiretroviral Drug Susceptibility With Primary HIV Infection in the United States", *6th Conference on Retroviruses and Opportunistic Infections*, Chicago, IL; Jan. 31–Feb. 4, 1999.

Rossero, R., et al., "Open Label Combination Therapy with Stavudine, Didanosine, and Hydroxyurea in Nucleoside Experienced HIV–1 Infected Patients", *5th Conference on Retroviruses and Opportunistic Infections*, Chicago, IL; Feb. 1–5, 1998.

Wegner, S., et al., "High Frequency of Antiretroviral Drug Resistance in HIV–1 from Recently Infected Therapy Naive Individuals", *6th Conference on Retroviruses and Opportunistic Infections*, Chicago, IL; Jan. 31–Feb. 4, 1999.

Bianchi, V., et al., "Changes of Deoxyribonucleoside Triphosphate Pools Induced by Hydroxyurea and Their Relation to DNA Synthesis", *The Journal of Biological Chemistry*, vol. 261, No. 34, Dec. 5, 1988, pp. 16037–16042.

ElAttar, et al, "Modulating effect of resvertol and quercetin on oral cancer cell growth and proliferation", pp. 187–193, (1999), Anti–Cancer Drugs, vol. 10, Lippincott Williams & Wilkins.

PCT Search Report for PCT/US00/22170 mailed Feb. 26, 2001.

* cited by examiner

COMPOSITIONS FOR TREATING VIRAL INFECTIONS, AND METHODS THEREFOR

The present application claims priority to U.S. Ser. No. 60/149,029 filed Aug. 13, 1999, the contents of which is incorporated by reference herein.

The present invention relates generally to the fields of medicine and virology. More particularly, it concerns methods and combination compositions for the treatment of viral infections, especially retroviral infections, for treatment of individuals who are treatment experienced and resistant to current protocols, and for post-exposure prophylaxis.

BACKGROUND OF THE INVENTION

Antiviral agents are generally modeled to inhibit viral replication within an infected cell. Effective antiviral agents specifically target steps within the viral replication pathway thereby inhibiting or hindering viral replication within infected host cells while having a minimal cytotoxic effect on the host. Thus, many antiviral agents are specific inhibitors to virus-specific enzymes or proteins, such as viral DNA or RNA polymerases, or cleavage enzymes for viral capsid protein. Nucleoside analogues, for example, have been developed that target particular enzymes in the viral replication pathway by mimicking a natural substrate of the enzyme.

Adverse toxicity effects exist with the administration of most antiviral agents, particularly at the dosage levels required to attain effective antiviral chemotherapy, due to a lack of viral specificity. Presently, there are very few antiviral agents that are considered to be efficacious, i.e. agents having a high level of viral toxicity and a low level of cytotoxicity. Such agents include iododeoxyuridine, adenine arabinoside and trifluorothymidine, all used to treat herpetic keratitis, acyclovir which is used in the treatment of genital herpes and mucosal and cutaneous herpes infections in the immunocompromised patient, and amantadine which is used to treat influenza A. These antiviral agents have a relatively low level of cytotoxicity in comparison to other antiviral agents. Adverse toxicity effects associated with acyclovir, for example, include transient impairment of renal function, nausea and vomiting, reversible neurological reactions, raised liver enzymes, rashes and increased hematological indexes.

Human immunodeficiency virus (HIV) is a prototype for pathogenic retroviruses, i.e., viruses that use reverse transcription to replicate. Reverse transcription mechanisms are required by those viruses having an RNA genome wherein the RNA is copied by a polymerase into DNA for subsequent replication. Certain DNA viruses use, in part, reverse transcription mechanisms to replicate such as, for example, hepatitis B virus. Reverse transcriptase is the virally-encoded polymerase used by retroviruses for this purpose.

Two nucleoside analogue reverse transcriptase inhibitors in combination with a potent protease inhibitor are generally recommended to achieve suppression of viral replication in current treatment protocols for HIV-1 infected individuals. Nucleoside analogue reverse transcriptase inhibitors in current use are described infra (adapted from Scientific American Medicine, January 1999, Chapter 11 www.samed.com, Scientific American Inc.).

Azidothymidine (AZT, zidovudine) is administered at a dosage of 600 mg orally daily in two divided doses. The major dose-limiting toxicity of AZT is on bone marrow. Clinical trials demonstrate that therapy delays clinical evidence of disease progression in previously untreated persons with CD4+T cell counts below 500 cells/mm$^3$. AZT is generally not used as a single agent.

Dideoxyinosine (ddI, didanosine) is administered orally as an inosine prodrug and is formulated with a buffer directed at gastric acid because of the acid lability of dideoxyadenosine. The major toxicities associated with ddI are pancreatitis and peripheral neuropathy. DdI was demonstrated to be superior to AZT in antiviral and immunomodulatory effects and to provide additional clinical benefits to patients who have used AZT.

Dideoxycytosine (ddC) is a nucleoside analogue reverse transcriptase inhibitor that exhibits potent antiretroviral activity in vitro. Dose escalation of ddC is limited by peripheral neuropathy, however, and ddC is therefore used only in combination regimens or for the treatment of patients who are intolerant of, or unresponsive to, other antiretrovirals. DdC is administered at a dosage of 0.75 mg three times daily and has been used extensively in combination regimens for persons with advanced AIDS who are intolerant of other antiretroviral chemotherapeutic agents.

D4T (stavudine), a thymidine analogue, has been investigated in patients with moderate to advanced HIV-1 infection, especially those with previous AZT experience. However, peripheral neuropathy is a major side effect.

Lamivudine (3TC) is well tolerated and results in acute reductions in plasma HIV-1 RNA levels. However, a single mutation in reverse transcriptase at position 184 results in a 100-fold to 1,000-fold decrease in susceptibility to lamivudine. Any measurable degree of viral replication in the presence of the drug results in the rapid emergence of resistant mutations. Lamivudine is associated with suppression of the erythroid and myeloid elements of bone marrow.

Abacavir is usually given as 600 mg, orally, daily in 2 divided doses. The drug is compromised by mutations in the reserve transcriptase (RT) gene. The efficacy of abacavir is compromised by the emergence of reverse transcriptase drug-resistant viral variants. In vitro studies have shown that the single mutations 65R, 74V, 184V, and 115F in the RT gene confer 2–3—fold decreases in susceptibility to abacavir. Mutants harboring 2 or 3 of these mutations exhibit approximately 10-fold resistance to the drug. In clinical studies, patients with more than 2 RT mutations showed a markedly inferior response to abacavir containing regimens.

F-ddA (lodenosine) is a fluorinated compound with similar structure and activity to ddI. F-ddA is not FDA-approved at the present time. Unlike ddI, stomach acids do not degrade F-ddA, so it can be administered without an antacid, thereby avoiding side effects attributable to the use of a buffer. Resistance to F-ddA is slow to emerge and the drug has shown in vitro activity against strains of HIV resistant to AZT, ddI, and ddC.

In light of rapid rates of viral replication, the highly error-prone HIV-1 reverse transcriptase, and the inability of currently available antiretroviral agents to completely inhibit HIV-1 replication, the development of resistance to antiretroviral drugs has been an inevitable consequence of drug exposure. Viral variants resistant to all antiretroviral agents in active use have been demonstrated (see the Scientific American Medicine, Chapter 11 cited herein, for a discussion of molecular mechanisms by which the virus may develop resistance to antiretroviral drugs).

The above-described protocols focus primarily on the interruption of the virus life cycle, through the inhibition of viral enzymes involved in viral replication. Though this has resulted in some control of the virus, over one-fourth of treatment naive individuals are infected with a virus with reduced susceptibility to one or more of the currently FDA-approved drugs. Moreover, up to 3% of newly diagnosed individuals are infected with a virus that is resistant to drugs in all types of currently approved therapies. Unfortunately, many of the current drugs in development are similar to currently existing therapies, and are likely to offer little to the current armamentarium of treatment.

Another approach to control HIV-1 replication is the targeting of cellular enzymes, a strategy based on the fact that the virus is dependent on the host cellular machinery for replication. Since host enzymes do not mutate at the same rate that viral proteins do, a cellular approach may result in controlling the emergence of drug-resistant viruses. Clinical trials using hydroxyurea and ddI have been reported in the treatment of HIV-1 infection (Lori, et al., JAMA, 277:1437–38, 1997; Vila, et al., Lancet, 348(9021:203–4, 1996). U.S. Pat. No. 5,736,527 relates to a method of treating HIV in humans by administration of ddI and hydroxycarbamide (hydroxyurea, (HU)), however, a mixture of hydroxycarbamide with AZT was found not to modify a viral replication profile compared to AZT alone. Clinical application of the combination of ddI and HU has been limited because of the antiproliferative and anti-DNA synthesis activity associated with HU. In addition, immunological reconsititution in patients that are responsive to the viral treatment is blunted. In patients with severe T-cell depletion, treatment with HU has resulted in increased bone marrow toxicity and CD4+T-cell depletion such that this combination is rarely used in patients with HIV-induced immunodeficiency. Toxicities possibly associated with HU, such as pancreatitis and increased liver function tests, highlight the need for new therapies in pursuing adjunctive antiretroviral therapy involving cellular enzyme inhibition or cell cycle modification.

A major target of HIV-1 is the CD4+T lymphocytes and monocyte-derived macrophages. It is thought that the majority of circulating lymphocytes are non-dividing, quiescent (resting) cells. Viral entry and transcription occur as efficiently in resting lymphocytes as in activated lymphocytes, but integration of the proviral DNA in the host genome only takes place in activated cells. Therefore, resting cells represent a major reservoir for HIV-1 infection and, upon cellular activation, constitute a source of new virus progeny. A large proportion of the HIV-1 genome in infected individuals exists as full length, extrachromosomal DNA, which retains the ability to integrate upon activation of the host cell. In addition, infected macrophages represent a long-term source of virus, since these cells do not die upon HIV-1 infection. Therefore, effective treatment protocols necessarily must address the presence of the virus in resting and long-term cellular reservoirs.

Retroviral, especially HIV, therapy is now thought to be a life-long process. Therefore, it is crucial to develop effective treatments that can be successfully administered for long periods of time for the suppression of retroviruses, and in particular, the prevention and/or inhibition of HIV. Further, it would be desirable to eliminate, or at least minimize, the cytotoxicity associated with the administration of antiviral agents otherwise determined to be effective. It is generally recognized that the toxicity of an antiviral agent may be avoided or at least minimized by administration of a reduced dose of the antiviral agent; however, it is also recognized that the effectiveness of an antiviral agent generally decreases as the dose is reduced.

Herpes simplex virus (HSV) types 1 and 2 are persistent viruses that commonly infect humans. HSV type 1 causes oral "fever blisters" (recurrent herpes labialis), and HSV type 2 causes genital herpes, which has become a major venereal disease in many parts of the world. Although it is uncommon, HSV can also cause encephalitis, a life-threatening infection of the brain. A most serious HSV-caused disorder is dendritic keratitis, an eye infection that produces a branched lesion of the cornea, which can in turn lead to permanent scarring and loss of vision. Ocular infections with HSV are a major cause of blindness.

Hepatitis is a disease of the human liver. It is manifested with inflammation of the liver and is usually caused by viral infections and sometimes by toxic agents. Hepatitis may progress to liver cirrhosis, liver cancer, and eventually death. Several viruses such as hepatitis A, B, C, D, E and G are known to cause various types of viral hepatitis. Among them, HBV and HCV are the most serious. HBV is a DNA virus and HCV is a RNA virus.

Hepatitis C is difficult to treat, and it is estimated that there are 500 million people infected with it worldwide. No effective immunization is currently available, and hepatitis C can only be controlled by preventive measures such as improvement in hygiene and sanitary conditions, and interruption of the route of transmission. At present, the only acceptable treatment for chronic hepatitis C is interferon which requires at least six months of treatment and/or ribavarin which can inhibit viral replication in infected cells and also improve liver function in some people. Treatment with interferon with or without ribavarin, however, has limited long term efficacy and has a low response rate.

Hepatitis B virus infection leads to a wide spectrum of liver injury. Moreover, chronic hepatitis B infection has been linked to the subsequent development of hepatocellular carcinoma, a major cause of death. Current prevention of HBV infection is a hepatitis B vaccination which is therapeutically effective. However, vaccination is not effective in treating those already infected (i.e., carriers and patients). Many drugs have been used in treating chronic hepatitis B and none have been proven to be effective, except interferon.

Treatment of HCV and HBV with interferon has limited success and has frequently been associated with adverse side effects such as fatigue, fever, chills, headache, myalgias, arthralgias, mild alopecia, psychiatric effects and associated disorders, autoimmune phenomena and associated disorders and thyroid dysfunction. Because the interferon therapy has limited efficacy and frequent adverse effects, a more effective regimen for the treatment of these viral infections is needed.

Because of the above problems in the art, current protocols are not completely satisfactory, and the present inventors provide improvements herein.

ABBREVIATIONS

AZT: zidovudine, 3'-azido-2',3'-dideoxythymidine, azidothymidine
ddA: 2',3'-dideoxyadenosine
ddC: 2',3'-dideoxycytosine
ddG: 2',3'-dideoxyguanosine
ddI: 2',3'-dideoxyinosine, didanosine
ddT: 2',3'-dideoxythymidine (DT4)
ELISA: Enzyme-linked immunoadsorbent assay
HIV: Human immunodeficiency virus
HU: Hydroxyurea
MDM: Monocyte-derived macrophage
PBMC: Peripheral blood mononuclear cell
PHA: Phytohemagglutinin
RNA: Ribonucleic acid
RV: Resveratrol

SUMMARY OF THE INVENTION

The present invention relates to a combination of an agent that promotes DNA synthesis in a virally-targeted cell in combination with a nucleoside analogue having antiviral activity, the administered combination for treating a viral infection in a subject in need thereof. Surprisingly, the present inventors have found that such a combination is minimally antiproliferative, yet has very potent antiviral activity. In particular, the invention relates to a method of treating, by preventing and/or inhibiting the spread of, retroviral infections, including HIV, by exposing a cell population, including cells infected by a retrovirus such as, for example, HIV, to such a combination. Further, the invention encompasses the treatment of HIV-infected and AIDS patients with such a combination in order to inhibit viral replication and HIV disease progression. A virally-targeted cell is a cell in which virus is present and is infective or potentially infective.

The present invention provides for the ability to suppress viral production for periods of time post-treatment, and to suppress nucleoside-resistant strains of virus in treatment-experienced subjects, with minimal toxicity. Furthermore, since one component of the combination compositions of the present invention targets cellular machinery of the host, rather than the virus, the present inventors expect that viral resistance to this drug combination essentially would not occur.

A method of treating a viral infection in a subject in need thereof, or for inhibition of a productive viral infection in a subject in need thereof by inhibition of viral production in a cellular reservoir of the subject is provided by the invention. The method comprises administering to the subject a combination of an agent that promotes DNA synthesis in a virally-targeted cell and a nucleoside analogue having antiviral activity. The method may further comprise the step of terminating the administering of the combination, thereby inducing a post-treatment period of viral incompetence.

A further aspect of the invention is a composition comprising a hydroxylated stilbene in an amount so as to provide an in vivo plasma concentration of 1 $\mu$M–25 $\mu$M and a nucleoside analogue having antiviral activity in an amount so as to provide an in vivo plasma concentration of 0.01 $\mu$M–100 $\mu$M.

Combination compositions of the present invention may comprise lower doses of the active antiviral nucleoside analogue while maintaining a level of antiviral activity that is characteristic of a higher dose. As a result, the cytotoxicity typically associated with the administration of an antiviral nucleoside analogue is minimized by the administration of combination compositions of the present invention. Combination compositions may comprise a usual dosage of antiviral nucleoside analogue in combination with a DNA synthesis-promoting agent to achieve a level of antiviral activity that is greater than that normally required while maintaining an acceptable level of cytotoxicity. An increased level of antiviral activity is useful particularly in the treatment of a viral infection caused by a strain that has developed a resistance to the administered nucleoside analogue.

The combination composition of the present invention demonstrates minimal antiproliferative activity, demonstrates enhancement of DNA synthesis activity at doses having antiviral activity, is useful for immunocompromised patients, and is useful for enhancing the in vivo capacity for immune reconstitution in a subject in need thereof.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE PREFERRED EMBODIMENTS

Figure 1:
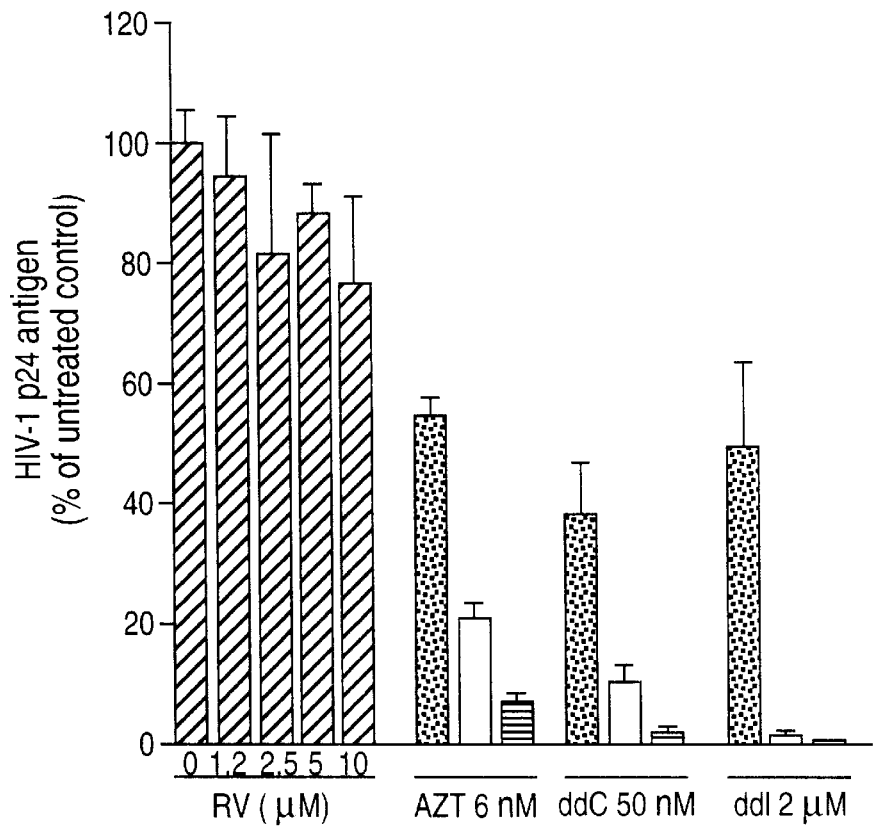
FIG. 1. Effect of RV in HIV-1 replication and its interaction with nucleoside analogs. PHA-activated PBMCs were infected with HTLV-IIIB and cultured in the presence of varying concentrations of RV with and without nucleoside analogs. HIV-1 replication was measured as % of p24 antigen in the culture supernatants on day 7 after infection as compared to the untreated control. Each data point reflects the mean+/−S.D. of duplicate wells. Dotted bars—no RV; open bars—RV, 5 $\mu$M; parallel-lined bars—RV, 10 $\mu$M.

The present inventors provide herein a preferred embodiment of the present invention, an enhancement of anti-HIV-1 activity of nucleoside analogs when administered in combination with a trihydroxystilbene, resveratrol, in in vitro assays known by those of skill in the art to be predictive of in vivo results. The greatest enhancement was obtained by the addition of 10 $\mu$M RV to 2 $\mu$M ddI, where a 200-fold increase in antiviral activity was shown in PHA-activated PBMCs infected with HTLV-IIIB. RV at 10 $\mu$M was not toxic to cells, and by itself reduced viral replication by 20–30%.

Similar antiviral activity was demonstrated when ddI was combined with 5 $\mu$M or 10 $\mu$M RV in PBMCs infected with clinical isolates of HIV-1. The addition of RV resulted in a greater than 10-fold augmentation of ddI-antiviral activity in infected monocyte-derived macrophages (MDMs). In a resting cell model of T-lymphocytes which were infected with HTLV-IIIB, RV plus ddI in combination, but not individually, suppressed the establishment of a productive viral infection. In addition, RV plus ddI markedly inhibited the replication of two ddI-resistant viral isolates, one containing the L74V reverse transcriptase (RT) gene mutation, the other containing 4 different resistance-associated mutations in the RT gene. Finally, when compared to hydroxyurea (HU), RV at 10 $\mu$M showed similar enhancement of ddI-antiviral suppressive activity as 100 $\mu$M HU, indicating that RV is significantly more potent than HU. RV was further shown to have less of a cellular antiproliferative effect than HU, demonstrating that RV is expected to have a better toxicity profile than HU. Unexpectedly, data infra demonstrate that RV promotes DNA synthesis while HU inhibits DNA synthesis. The present inventors, therefore, provide herein a DNA synthesis-promoting agent in combination with a nucleoside analog having antiviral activity for treatment of a subject in need thereof.

The eukaryotic cell cycle includes cell growth (interphase) and division (mitosis) that takes place in four phases: G1 phase, gap 1, prior to DNA synthesis; S phase, period of DNA synthesis; G2 phase, gap 2, between DNA synthesis and mitosis; and M phase, mitosis. The length of these periods depends upon the cell type and conditions of growth. Mitosis is usually the shortest phase. Resveratrol blocks cells at the S/G2 phase transition resulting in the elongation of the S phase (Ragione, et al., BBRC 250:53–58, 1998).

Cell types that do not divide are considered to have withdrawn from the cell cycle into a non-proliferative state, resembling G1 but distinct from it because they are unable to proceed into S phase. This noncycling quiescent state is called G0. In the case of CD4+T-lymphocytes, these cells emerge from the thymus as naive cells and circulate until they encounter antigen. They then undergo blast transformation and begin to proliferate. Some of the cells survive and return to a G0 resting state in which they persist as memory cells able to respond again to subsequent encounters with the same antigen. In the case of monocytes, these cells originate in the bone marrow and enter the bloodstream. Circulating monocytes migrate into extravascular tissues where they differentiate into macrophages. Monocytes and macrophages normally do not divide, and remain in the G0 phase of the cell cycle.

Nucleoside analogues, e.g., AZT and ddC, must be phosphorylated to their active nucleotide forms by cellular kinases in order to be effective in inhibitory activity. The level of required kinases varies in the cell during the cell cycle, however, they are elevated during the S phase. While not wanting to be bound by theory, the present inventors believe that the elevated levels of the required kinases coupled with the added time in S phase may serve to create an environment where certain nucleoside analogues, e.g., AZT and ddC, can better be converted to their active states.

In a preferred embodiment of the invention, the nucleoside analogue ddI is combined with resveratrol. Phosphorylation of ddI is catalyzed by a 5'-nucleotidase that is not cell-cycle dependent. The 5' nucleotidase (phosphotransferase) uses IMP as the major phosphate donor, and high intracellular IMP levels correlate with an increase in the phosphorylation of ddI. Growth arrested cell lines have increased amounts of IMP due to decreased activity of the enzymes adenylosuccinate synthetase and IMP dehydrogenase. While not wanting to be bound by theory, the present inventors believe that the cytostatic activity of RV, resulting in prolongation of the S phase, may also result in increased IMP levels, and therefore, increased phosphorylation rates of ddI by 5'nucleotidase.

In contrast to resveratrol, hydroxyurea blocks cells at the G1/S phase transition, thereby preventing cells from entering the S phase (Bianchi et al., 1986. J. Biol Chem. 261:34, 16037; and Young et al., Cancer Research 27:535, 1967).

While Fontecave et al. (FEBS Letters 421:277–279, 1998) report that resveratrol is an inhibitor of ribonucleotide reductase, and of DNA synthesis in K-562 human myelogenous leukemia cells and in P-815 murine mastocytoma cells, results provided infra by the present inventors surprisingly demonstrate that resveratrol promotes DNA synthesis in peripheral blood mononuclear cells. While not wanting to be bound by theory, the present inventors believe that the unexpected effectiveness of the combination of compounds provided herein may be due to stimulation of DNA synthesis together with incorporation of a nucleoside analog.

Subject in need thereof: As used herein, "subject in need thereof," is a mammal, in particular, a human, infected with a virus in which incorporation of a nucleoside analogue has antiviral activity. In a preferred embodiment, the virus uses a reverse transcription mechanism wholly or in part for replication. The subject, in a preferred embodiment, is a treatment-experienced mammal having resistance to currently employed nucleoside analogues, or a mammal at risk for becoming infected due to exposure by known and well-accepted transmission routes. The subject may or may not have seroconverted. In particular, the virus is a retrovirus, such as an oncovirus HTLV-I or II, or such as a lentivirus visna or human immune deficiency virus HIV-1 or HIV-2, or the like. The virus may also be a DNA virus. In particular, the virus may use reverse transcription mechanisms for replication such as the hepatitis B virus, for example.

A subject in need thereof may be a perinatal subject, or an immune deficient subject. A perinatal subject is a pregnant individual during the period of time surrounding the birth of a baby. An immune deficient subject has a lower than normal CD4+T-cell count, a normal count being about 800–1000/mm$^3$. A subject having advanced immune deficiency may have a CD4+T-cell count of less than about 200/mm$^3$. An unexpected result of the present combination composition is that immune reconstitution is made possible, i.e., the CD4+ T-cell count may increase to a value at or near normal levels.

Method of Treating a Viral Infection: A method of treating a viral infection is meant herein to include "prophylactic" treatment or "therapeutic" treatment. A "prophylactic" treatment is a treatment administered to a subject who does not exhibit signs of a disease or who exhibits early signs of the disease for the purpose of decreasing the risk of developing pathology associated with the disease. A "therapeutic" treatment is a treatment administered to a subject who exhibits signs of pathology for the purpose of diminishing or eliminating those signs. A "therapeutically effective amount" of a compound is that amount of compound that is sufficient to provide a beneficial effect to the subject to which the compound is administered. A beneficial effect means rendering virus incompetent for replication, inhibition of viral replication, inhibition of infection of a further host cell, or increasing CD4+T-cell count, for example.

A virally-targeted cell: As used herein, "a virally-targeted cell" means a cell in which virus is present and is infective or potentially infective and includes epithelial cells, nervous system cells, T-lymphocytes (activated or resting), macrophage, monocytes, tissue dendritic cells or the like. A virus includes any virus susceptible to a nucleoside analogue, and includes DNA and RNA viruses, i.e., herpes, hepatitis, influenza, immunodeficiency viruses, cytomegalovirus, or the like.

Agent that promotes DNA synthesis: The present inventors have discovered that an agent that promotes DNA synthesis when used in combination with a nucleoside analog is unexpectedly effective for preventing a productive viral infection. A test for an agent that promotes DNA synthesis is as follows. A candidate agent is incubated in a DNA synthesis assay where the amount of $^3$H-thymidine incorporation into newly synthesized DNA is compared to a control assay in the absence of candidate agent. A greater amount of $^3$H-thymidine uptake in the presence of the candidate agent as compared to its absence indicates an agent that promotes DNA synthesis. For example, a thymidine incorporation assay using PBMC's may be carried out as follows. PBMC's are suspended, then 0.1 ml (100,000) of cells are added to each designated well of a 96-well plate. The plates are placed into a 37° C., 5% $CO_2$, 95% humid incubator for the predetermined incubation periods—normally 2 and 5 days. At the end of the incubation period, and at a standard time prior to harvesting the plate (6–18 hours), 1.0–1.5 μCi (20 μl of 50–75 mCi/ml in complete medium) of [$^3$H]-labeled methyl thymidine is added to each well of the assay. The plates are then incubated for the remaining 6–18 hours. At the end of the [$^3$H]-thymidine pulse, the plates are harvested onto filter paper using a semi-automated multi-well harvester. The filter paper containing bound DNA may be dried using either ethanol or by moderate microwave heating. The filter paper samples are counted in a scintillation counter using standard procedures.

Among agents that promote DNA synthesis, hydroxylated stilbenes, particularly the dihydroxystilbenes, the trihydroxystilbenes, and the tetrahydroxystilbenes are preferred. Hydroxylated stilbene derivatives and hydroxylated-stilbene-containing natural products are also contemplated by the present inventors as agents that promote DNA synthesis. A particularly preferred trihydroxystilbene is resveratrol (RV)(trans-3, 4', 5-trihydroxystilbene). Resveratrol is a natural phytoalexin present in the skin of grapes (esp. red grapes), peanuts, mulberries, numerous plants and trees, and has been reported to protect against atherosclerosis, certain cancers, and inflammation. Its apparent function in the plant kingdom is as a defensive mechanism against environmental stress and pathogens. RV is also present in a number of plants used in traditional Asian medicine, and is an ingredient in several over-the-counter vitamin supplements. Therefore, resveratrol or derivatives thereof are available as extracts or powders of natural products, mainly extracted from Vitaceae species and particularly from the skin, grapes, grape-seeds, grape-stalks, and leaves of grapevines. Its concentration is greater in grape plants affected by typical diseases of the vine.

Further sources of resveratrol or derivatives thereof may include extracts of the root, rhizome, stalk, leaf, fruit, cotyledon, or seed of sources such as Vitaceae, Umbellifereae, Myrtaceae, Dipterocarpaceae, Cyperaceae, Gnetaceae, Leguminosae, cereals, Sericeae, Haemodoraceae, Musaceae, Polygonacea, Pinaceae, Cupressaceae, Cesalpiniaceae, Poaceae, or Solanaceae, for example.

Resveratrol is commercially available from Sigma (St. Louis, Mo.) and from Pharmscience as RESVERIN™ (Montreal, Quebec, Canada). As used herein, reference will be made to resveratrol, with the understanding that whatever is disclosed in connection with resveratrol is expected by the present inventors to apply to dihydroxystilbenes, trihydroxystilbenes, tetrahydroxystilbenes, salts thereof, cis- and trans-isomers thereof, stereoisomers, enantiomers, regioisomers, diasteromers, oligomers thereof, polymers thereof, derivatives thereof, and to plant or herbaceous extracts containing such DNA synthesis promoting agents. Particularly preferred derivatives of resveratrol include alkyl, alkoxy derivatives such as pterostilbene (trans-3,5-dimethoxy-4'-hydroxystilbene), or carbohydrate derivatives such as the glycoside derivative, 3,4',5-trihydroxystilbene-3-β-mono-D-glucoside (trans-polydatin, piceid). Further trihydroxystilbenes provided for methods and compositions of the present invention include trans-3,3',5-trihydroxystilbene, trans-3,4,4'-trihydroxystilbene, 3,3',5-trihydroxy-4'-methoxystilbene-3-O-β-D-glucoside (Rhapontin, Sigma) or the like.

Tetrahydroxystilbenes contemplated for methods and compositions of the present invention include trans-3,3',4,5'-tetrahydroxystilbene (piceatannol, Sigma, St. Louis Mo.), trans-3,3', 5,5'-tetrahydroxystilbene, or the like. A dihydroxystilbene is 3,5-dihydroxystilbene (pinosylvin).

PCT publication WO 99/03816 is incorporated by reference herein for disclosure of resveratrol compositions and preparation thereof.

Included within the scope of an agent that promotes DNA synthesis in a virally-targeted cell for the present invention are in vivo metabolites of the agent promoting DNA synthesis, and prodrugs. As used herein, an in vivo metabolite is a product that results from an in vivo biological process. As used herein, a "prodrug" is a drug covalently bonded to a carrier wherein release of the drug occurs in vivo when the prodrug is administered to a mammalian subject. Prodrugs of the compounds of the present invention are prepared by modifying functional groups present in the compounds in such a way that the modifications are cleaved, either in routine manipulation or in vivo, to yield the desired compound. For example, prodrugs include compounds wherein hydroxy groups are bonded to any group that, when administered to a mammalian subject, is cleaved to form the free hydroxyl. Examples of prodrugs include, but are not limited to, acetate, formate, or benzoate derivatives of alcohol functional groups in the compounds of the present invention; phosphate esters, dimethylglycine esters, aminoalkylbenzyl esters, aminoalkyl esters or carboxyalkyl esters of alcohol or phenol functional groups in the compounds of the present invention, or the like.

The concentration of a particular hydroxylated stilbene may be determined in plasma using HPLC analysis and comparison of the resultant chromatographic profile with that of standard hydroxylated stilbene compounds.

Nucleoside Analogue having antiviral activity: The term "nucleoside analogue having antiviral activity" as used herein, means a nucleoside analogue that has inhibitory activity for a virus. Nucleoside analogues include analogues of both purine (i.e., adenine and guanine) and pyrimidine (i.e. thymine, uracil and cytosine) nucleosides.

Preferred nucleoside analogues of the present invention include, but are not limited to, the following.

acycloguanosine (acyclovir) adenine arabinoside iododeoxyuridine trifluorothymidine (1C, CiS)-4-(2-amino-6-(cyclopropylamino)—9H-purin-9-yL)-2-cyclopentene-1-methanol sulfate (salt) (2:1)(abacavir)

2',3'-dideoxy-3'-azidouridine

2'-3'-dideoxyinosine (ddI)

2'-3'-dideoxyguanosine (ddG)

2'-3'-dideoxycytidine (ddC)

2'-3'-dideoxyadenosine (ddA)

2'-deoxy-3'-thiacytidine (3TC, lamivudine)

3'-deoxythymidine (ddT)

2'-3'-dideoxy-2',3'-didehydro-$N^6$-(O-methylbenzyl) adenosine

2'-3'-dideoxy-2',3'-didehydro-$N^6$-(2-methylpropyl) adenosine

2',3'-dideoxy-3'-azidoguanosine

3'-deoxy-3'-azidothymidine (AZT)

2',3'-dideoxy-3'-fluoro-5-chlorouridine

3'-deoxy-3'-flourothymidine

2',3'-dideoxy-3'-fluoroadenosine (F-ddA, lodenosine)

2',3'-dideoxy-3'-fluoro-2.6-diaminopurineriboside

2',3'-dideoxy-2'-3'-didehydrocytidine

3'-deoxy-2',3'-didehydrothymidine (d4T, stavudine)

A test for "a nucleoside analogue having antiviral activity" is, for example, an assay for the amount of p24 antigen produced in the presence or absence of the nucleoside analogue being tested in HIV-1 infected PBMCs as taught herein, for example. A lower amount of p24 antigen present in a test assay as compared to a control assay indicates a nucleoside analogue having said activity.

Mannose derivatives of the nucleoside analog or of the DNA synthesis-promoting agent compositions of the present invention are contemplated for the present invention, in particular, since macrophage possess receptors for D-mannose that would enable such molecules to be preferentially taken up by macrophage.

Included within the term "nucleoside analog," as used herein, is the nucleotide derivative thereof, i.e., the mono, di or triphosphate derivative. It is well known by those of skill in the art that "unshielded" triphosphates cannot be used directly as drugs because triphosphates do not penetrate cell membranes, and that the triphosphate is the form incorporated into nucleic acid. One embodiment of the invention is the direct delivery of the triphosphate derivative to the host cells as described infra, e.g., liposomal delivery, or the like. Nucleotide analogs under development include cidofovir (vistide), adefovir (preveon), and the oral prodrug form of PMPA, known as bis-POC-PMPA.

Dosages: Doses to be administered are variable according to the nucleoside analogue to be used, the DNA synthesis-promoting agent to be used, the treatment period, frequency of administration, the host, and the nature and severity of the infection. The dose can be determined by one of skill in the art without an undue amount of experimentation. The compositions of the invention are administered in substantially non-toxic dosage concentrations sufficient to ensure the release of a sufficient dosage unit of the present combination into the patient to provide the desired inhibition of the virus. A substantially non-toxic dosage is minimally antiproliferative and has an immune reconstitution profile more promising than current protocols. The actual dosage administered will be determined by physical and physiological factors such as age, body weight, severity of condition, and/or clinical history of the patient. The active ingredients are ideally administered to achieve in vivo plasma concentrations of a nucleoside analogue of about 0.01 $\mu$M to about 100 $\mu$l, more preferably about 0.1 to 10 $\mu$M, and most preferably about 1–5 $\mu$M, and of a DNA synthesis-promoting agent of about 1 $\mu$M–25 $\mu$M, more preferably about 2–20 $\mu$M, and most preferably about 5–10 $\mu$M.

For example, in the treatment of HIV-positive and AIDS patients, the methods of the present invention may use compositions to provide from about 0.005–500 mg/kg body weight/day of nucleoside analog, more preferably from about 0.1–200 mg/kg/day, and most preferably 1–50 mg/kg/day; and from about 0.01–1000 mg/kg body weight/day of a DNA synthesis-promoting agent, more preferably from about 0.1–100 mg/kg/day, or most preferably from about 0.5–50 mg/kg/day. Particular unit dosages of a DNA synthesis-promoting agent and a nucleoside analog of the present invention include 50 mg, 100 mg, 200 mg, 500 mg, and 1000 mg amounts, for example, formulated separately, or together as discussed infra.

In accordance with the specific embodiments disclosed herein, appropriate dosages of resveratrol and AZT for administration in the treatment of a subject in need thereof range from about 100 to about 5000 $\mu$g nucleoside analogue in combination with from about 10 to about 15,000 $\mu$g resveratrol per kilogram mammalian body weight. Further, dosages of AZT and resveratrol suitable for treating mammals infected with HIV, range from about 100 to about 1000 $\mu$g AZT per kilogram mammalian body weight and from about 10 to about 5,000 $\mu$g or, more preferably, 10 to about 300 $\mu$g resveratrol per kilogram mammalian body weight. Particularly preferred dosages of AZT and resveratrol are those dosages at the lower end of these ranges. A specific example of a preferred dosage is about 100 $\mu$g AZT per kg administered in conjunction with about 50 $\mu$g resveratrol per kg. It will be understood, however, that dosage levels that deviate from the ranges provided may also be suitable in the treatment of a given viral infection. Weight ratios of agent to analogue or analogue to agent may range from 1:1 to 1:1000, or 1:1 to 1:500, or 1:1 to 1:100, or 1:1 to 1:10.

In treating a mammal in need thereof, a therapeutically effective amount of the present composition is administered thereto in accordance with the present invention. As used herein, the term "therapeutically effective amount" is an amount of the composition indicated for treatment while not exceeding an amount which may cause significant adverse effects. Methods for evaluating the effectiveness of combinations of the present invention include PCR-based assays for viral RNA in plasma. Kits including appropriate PCR primer pairs are available commercially, e.g., from Chiron Corporation, (Emeryville, Calif.), Roche (Boehringer-Mannheim), and Ortho (Netherlands). The CD4+T cell count is the most useful indicator of immunologic dysfunction and the immediate risk for opportunistic infections, whereas the level of HIV-1 RNA in plasma is the best predictor of the rate of clinical and immunologic progression.

The dose is modified according to the patient's hepatic, renal and bone marrow function, functions which are frequently abnormal in patients with viral infections. One may wish to use a higher dose of compositions of the present invention for therapy of certain manifestations of HIV infection, e.g., HIV-related dementia.

The relative amounts of nucleoside analogue and DNA synthesis-promoting agent required to form a combination composition of the present invention are determined using assays conventional in the art. Thus, cells infected with a virus, against which a given nucleoside analogue is active, are subjected to varying concentrations of that nucleoside analogue in the presence of varying concentrations of a DNA synthesis-promoting agent. In this way, the various combinations of concentrations of nucleoside analogue and DNA synthesis-promoting agent that form combination compositions can be determined by observing subsequent viral replication and comparing results thereof. Thus, as described herein, the relative amounts of the nucleoside analogue, ddI, and resveratrol required to form a combination composition of inhibiting HIV-1 are determined by incubating cells infected with HIV-1 in the presence of varying concentrations of ddI and resveratrol. From these analyses, dosages effective to treat a virally-infected mammal can be determined in an established manner.

Formulations and Administration: Combination compositions of the present invention may be in any form suitable for co-administration separately or as an admixture. Such administrable forms include tablets, buffered tablets, pills, capsules, enteric-coated capsules, dragees, cachets, powders, granules, aerosols, liposomes, suppositories, creams, lotions, ointments, skin patches, parenterals, lozenges, oral liquids such as suspensions, solutions and emulsions (oil-in-water or water-in-oil), ophthalmic liquids and injectable liquids, or sustained-release forms thereof. The desired dose may be provided in several increments at regular intervals throughout the day, by continuous infusion, or by sustained release formulations, or may be presented as a bolus, electuary or paste.

Combination compositions of the present invention may be administered alone in solution. In one embodiment, compositions of the present invention are prepared by admixture of a DNA synthesis-promoting agent and an antiviral nucleoside analogue of the present invention and a pharmaceutically acceptable carrier. As used herein, "pharmaceutically acceptable" means acceptable for use in the pharmaceutical and veterinary arts, compatible with other ingredients of the formulation, and not being toxic or otherwise unacceptable.

The selection of carrier depends on the intended mode of administration of the combination composition. Thus, compositions to be administered orally are prepared using substances that are suitably combined with a DNA synthesis-promoting agent and/or the nucleoside analogue for oral ingestion. Such substances include, without limitation, sugars, such as lactose (hydrous, fast flow), glucose and sucrose; starches such as corn starch and potato starch; cellulose and derivatives thereof, including microcrystalline cellulose, sodium carboxymethylcellulose, ethylcellulose and cellulose acetates; powdered tragacanth; colloidal silicon dioxide; croscarmellose sodium; malt; gelatin; talc; stearic acids; magnesium stearate; calcium sulfate; vegetable oils, such as peanut oils, cotton seed oil, sesame oil, olive oil and corn oil; polyols such as propylene glycol, glycerine, sorbitol, mannitol and polyethylene glycol; agar; alginic acids; antacids such as aluminum hydroxide or magnesium hydroxide; buffer such as sodium citrate, acetate, or bicarbonate; water; isotonic saline and phosphate buffer solutions. Wetting agents, lubricants such as sodium lauryl sulfate, stabilizers, tabletting agents, anti-oxidants, preservatives, coloring agents and flavoring agents may also be present.

Formulations suitable for parenteral administration include aqueous and non-aqueous, isotonic sterile injection solutions which may contain antioxidants, buffers, bacteriostats or solutes which render the formulation isotonic with blood; and aqueous and non-aqueous sterile suspensions which may include suspending agents and thickening agents. The formulations may be presented in unit-dose or multi-dose sealed containers, for example, ampoules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules or tablets, or the like. Likewise, compositions for ophthalmic administration are prepared in suitable liquid carriers such as buffered or physiological saline, liposomes or basic amino acids. Creams, lotions and ointments may be prepared for topical application using an appropriate base such as triglyceride base, liposomes, or basic amino acids. Such creams, lotions and ointments may also contain a surface active agent.

A pharmaceutical composition of the invention can take the form of a lyophilized powder of the active substance, to be dissolved immediately before use in a physiological solution for the purpose of injection.

Compositions of the present invention may be administered parenterally, intravenously, intraperitoneally, intraosseously, in the cerebrospinal fluid, or the like. Further modes of administration include rectal, nasal, buccal, sublingual, vaginal, subcutaneous, intramuscular, or intradermal administration.

In another embodiment of the present invention, the antiviral nucleoside analogue and DNA synthesis-promoting agent are administered in separate compositions rather than administered admixed in a single composition. This is particularly preferred when the desired mode of administration of the nucleoside analogue and DNA synthesis-promoting agent differ. Thus, a composition comprising an antiviral nucleoside analogue is prepared by admixture of the analogue with at least one suitable pharmaceutically acceptable carrier to achieve an antiviral nucleoside analogue composition in the desired administrable form. Likewise, a composition comprising a DNA synthesis-promoting agent is prepared by admixture with at least one suitable pharmaceutically acceptable carrier to achieve a composition in the desired administrable form. The nucleoside analogue and DNA synthesis-promoting agent compositions may be administered together as an admixture, administered separately but concurrently, or separately but substantially concurrently, at appropriate dosage levels.

For a perinatal subject, the drug combination of the present invention may be, for example, administered orally after 36 weeks of pregnancy and continued through delivery. Interventions around the time of late gestation and delivery (when the majority of transmissions are thought to occur) are most efficacious.

A pharmaceutical combination in kit form may be provided which includes in packaged combination a carrier means adapted to receive a container means in close confinement therewith and a first container means including a pharmaceutical nucleoside analogue composition and a pharmaceutical DNA synthesis-promoting agent composition. In such a kit, the nucleoside analogue and DNA synthesis-promoting agent compositions may be in different administrable forms. For example, the DNA synthesis-promoting agent may be in an orally administrable form such as tablet, pill, capsule or powder form, while the nucleoside analogue composition may be in a form suitable for administration by injection, i.e., in solution form. Such kits can further include, if desired, one or more of various conventional pharmaceutical kit components, such as, for example, containers with one or more pharmaceutically acceptable carriers, additional containers, etc., as will be readily apparent to those skilled in the art. Printed instructions, either as inserts or as labels, indicating quantities of the components to be administered, guidelines for administration, and/or guidelines for mixing the components, can also be included in the kit.

The present invention also includes use of combination compositions as presented herein further in combination with other medical compositions intended for the treatment of those viral infections set forth herein.

The following examples are included to demonstrate preferred embodiments of the invention. However, those of skill in the art should, in light of the present disclosure, appreciate that changes can be made in the specific embodiments which are disclosed and still obtain a like or similar result without departing from the spirit and scope of the invention.

EXAMPLE 1

Resveratrol Enhances the Antiviral Activity of Nucleoside Analogs in Activated PBMCs The antiviral activities of RV alone and in combination with nucleoside analogs were investigated in PHA-stimulated PBMCs from seronegative donors. RV, ddC, ddI, and AZT were purchased from Sigma (St. Louis, Mo.). The HIV-1 T-cell line adapted isolate HTLV-IIIB was obtained from Dr. Gallo, at the National Institutes of Health AIDS Research and Reference Reagent Program (Catalog #398, Rockville, Md.). Primary strains of HIV-1 were isolated by coculturing $10^7$ patient PBMC with an equal number of PHA-stimulated PBMC from a normal donor. Titration of stocks and MT-2 phenotype determination were carried out as described (ACTG Virology Manual, NIH Pub No. 94 3828, 1994). The SI phenotype was determined by assessing viral growth and syncytia formation in the MT-2 cell line obtained from Dr. Richman at the National Institutes of Health AIDS Research and Reference Reagent Program (Catalog #237, Rockville, Md.).

Primary PBMCs were separated from whole blood of HIV seronegative donors by density centrifugation over Ficoll-Hypaque (Sigma). The culture medium consisted of RPMI supplemented with 10% fetal bovine serum (FBS), 2 mM glutamine and penicillin/streptomycin (Gibco, Grand Island, N.Y.).

For infection studies involving PBMCs, cells were stimulated with 2.5 or 10 µg/ml phytohemagglutinin (PHA; Boehringer Mannheim, Indianapolis, Ind.) for 3 days. Stimulated PBMCs were infected by incubation with virus at a multiplicity of infection of 1000 $TCID_{50}/10^6$ PBMC for 2 hours. PBMCs were then washed three times with PBS and cultured in 5% $CO_2$ at 37° C., in RPMI/10% FBS supplemented with 10 units/ml IL-2 (Boehringer Mannheim) and drugs as appropriate. PBMCs were seeded in 96-well flat-bottom plates at a density of $2 \times 10^5$ PBMCs/200 µl. Following 3 days of culture half of the medium was replaced with fresh medium containing IL-2 and drugs. After 7 days of culture, HIV-1 p24 antigen production in the culture supernatant was assayed by ELISA (Coulter, Hialeah, Fla.). The concentration of nucleoside analog, alone and in combination with resveratrol, that reduced the p24 antigen value of the untreated control by 90% ($IC_{90}$) was calculated by using nonparametric regression analysis. The analysis used the median-effect equation, $Fa=1/[1+(D_m/D)]^m$, where D is the dose, Fa is the fraction affected, and $D_m$ is the dose required to produce the median effect.

Figure 2:
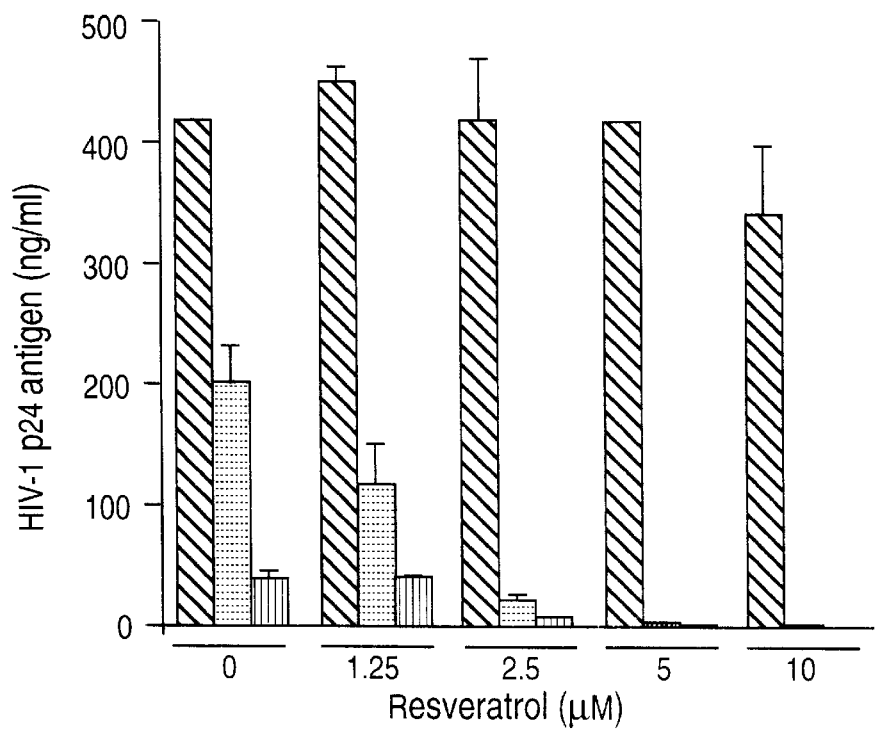
FIG. 2. Inhibition of HTLV-IIB replication by RV and ddI. PHA-activated PBMCs were infected and then cultured in the presence of various concentrations of RV and ddI. Day 7 p24 antigen values of the supernatants are shown. Each data point reflects the mean+/−S.D. of triplicate wells. Diagonally-lined bars—no ddI; shaded bars—ddI, 2 $\mu$M; vertically-lined bars—ddI, 4 $\mu$M.

Cells were infected with the T-cell tropic isolate HTLV-IIIB for 2 hours, and then cultured in varying concentrations of RV with or without nucleoside analogs. Virus replication was measured by p24 antigen production by ELISA using a standard commercial kit in the culture supernatants on days 7 and 10 after infection. Peak virus production occurred on day 7. Data are provided in FIGS. 1, 2, and 14–16. At the tested concentrations, RV alone had little effect on HIV-1 replication. RV (5 µM) reduced virus production by approximately 10%, however, it enhanced the antiviral effect of the nucleoside analogs at the tested concentrations. As a result, the $IC_{90}$ values of AZT, ddC and ddI were reduced 1.6-fold (from 0.025 to 0.015 µM)), 3.3-fold (from 0.27 to 0.08 µM) and 5.7-fold (from 7.5 to 1.3 µM), respectively. A greater potentiation in antiviral activity was observed when the nucleoside analogs were combined with 10 µM RV, a concentration that by itself inhibited viral replication by approximately 30%. In the presence of 10 µM RV, the $IC_{90}$ values of AZT, ddC and ddI were reduced 3.1-, 5.4-, and 17.8-fold, respectively. Anti-HIV activity for RV in the absence of, and in combination with, 2 µM and 4 µM ddI is shown in FIG. 2.

The data demonstrate that a lower dosage of nucleoside analogue when combined with RV may produce a therapeutic antiviral response equivalent to a higher dosage of the analogue alone, thus, reducing toxicity of the analogue.

EXAMPLE 2

Resveratrol Enhances the Antiviral Activity of Nucleoside Analogs in Clinical Isolates The increase of ddI-antiviral activity by RV was next evaluated in a panel of clinical isolates of HIV-1. Clinical isolates EJC-1 to EJC-4 were obtained under an approved human studies protocol from infected individuals followed at the University of Maryland Medical Center, Baltimore, Md.

Figure 3:
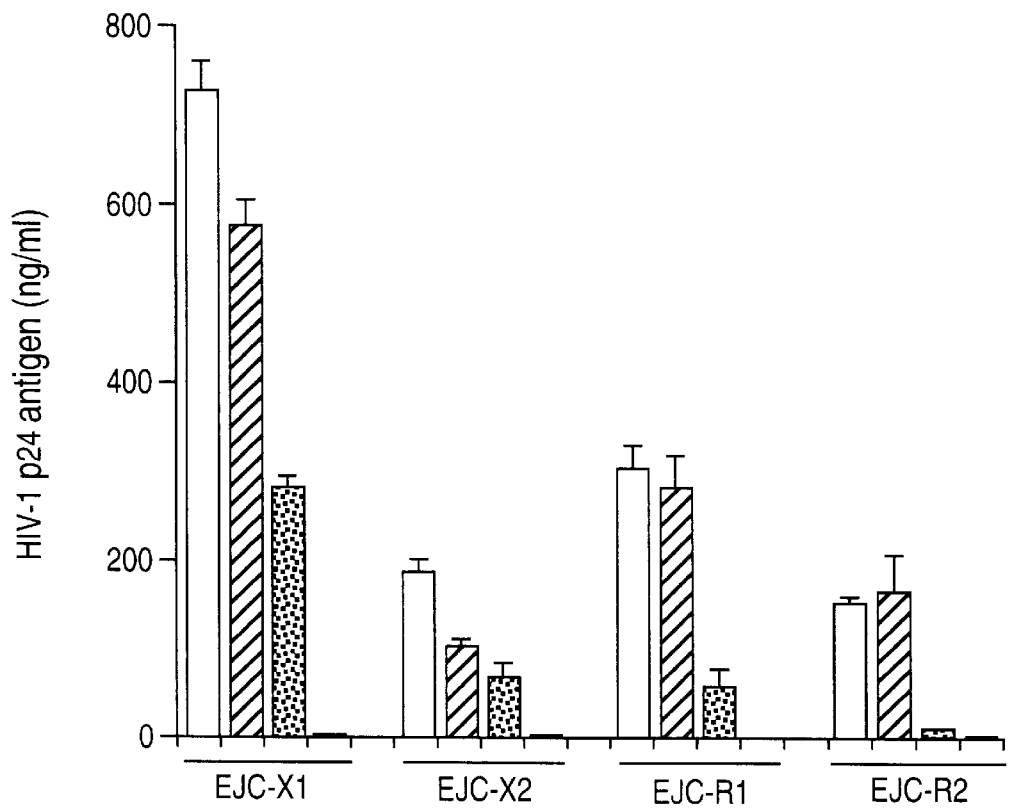
FIG. 3. Inhibition of viral replication in HIV-1 clinical isolates with RV plus ddI. PHA-activated PBMCs were infected with clinical isolates and cultured in the presence of RV and ddI. Day 7 p24 antigen values of the supernatants are shown. Each data point reflects the mean+/−S.D. of duplicate wells. Open bars—no drug; diagonally-lined bars—resveratrol, 5 $\mu$M; dotted bars—ddI, 1 $\mu$M; solid bars—ddI, 1 $\mu$M+resveratrol, 5 $\mu$M.

PBMCs, activated as provided in Example 1, were infected with different virus isolates and cultured in the presence of 1 µM ddI plus 5 µM or 10 µM RV. Results obtained with 5 µM RV are expressed as p24 antigen/$10^6$ viable cells to further demonstrate that the antiviral effect is not due to antiproliferative activity (FIG. 3). At 5 µM RV there was enhanced antiviral activity of ddI by 18–185-fold depending on the clinical isolate. At 10 µM an even more potent effect was observed resulting in an enhancement of ddI activity by 88–1200-fold.

EXAMPLE 3

Inhibition of HIV-1 Replication in Monocyte-Derived Macrophages

To investigate whether RV also enhanced the activity of ddI in macrophages, monocyte-derived macrophages (MDMs) from 2 different seronegative donors were infected with the macrophage-tropic isolate HIV-$1_{SF162}$. MDMs were prepared as described infra, and infected with the SF162 strain of HIV-1 obtained from Dr. Levy at the National Institutes of Health AIDS Research and Reference Reagent Program (Rockville, Md.). Briefly, $25 \times 10^6$ freshly isolated PBMCs were cultured for 5 days in T-25 flasks (Coming Costar, Cambridge, Mass.) containing culture medium supplemented with 20% FBS and 10% AB human serum (Gemini Bioproducts, Inc., Calabasas, Calif.). On day 5, non-adherent cells were removed by washing five times with warm RPMI/10%FBS medium. Adherent cells in representative flasks were counted by trypan blue exclusion. By morphology and cytochemical staining for nonspecific esterase (Sigma), more than 97% of cells were macrophages. HIV infection was carried out by adding virus to the flask at a multiplicity of infection of 2000 $TCID_{50}/10^6$ adherent cells and incubating for 3 hours. Flasks were then washed 3 times with warm RPMI/10%FBS medium and cultured in RPMI containing 20% FBS plus drugs. Every 3 days culture supernatants were collected and fresh medium containing drugs was added to each flask. Virus replication was assayed weekly for p[24] antigen production as described in Example 1 in the supernatant. Cultures were maintained for 3 weeks.

Figure 4:
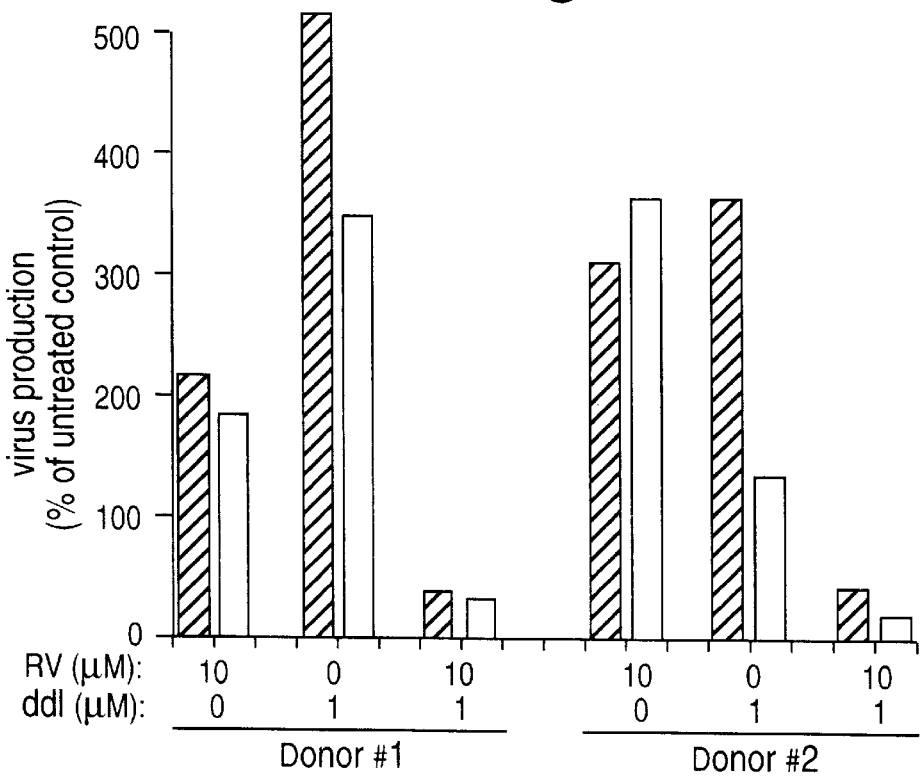
FIG. 4. Antiviral effect of RV and ddI in monocyte-derived macrophages (MDMs). MDMs derived from 2 HIV-seronegative donors were infected with HIV-1$_{SF162}$, and then cultured in the presence of RV and ddI. Virus production was assayed on days 7 and 16 after infection and compared to that obtained in the infected MDMs not exposed to drugs. Diagonally-lined bars—day 7; open bars—day 16.
Figure 17:
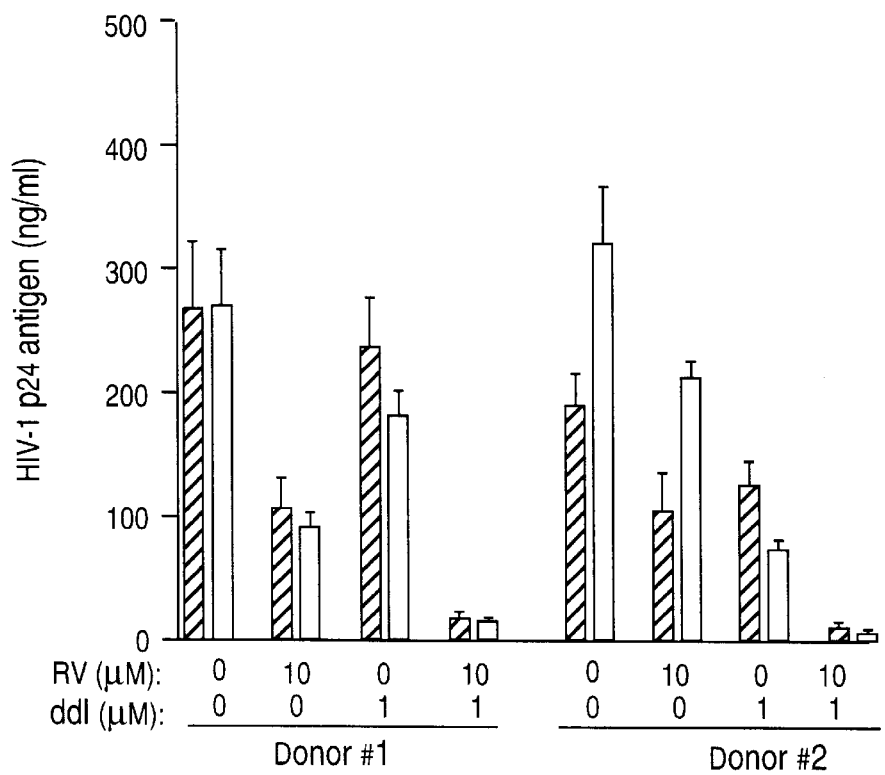
FIG. 17. Antiviral effect of RV and ddI in monocyte-derived macrophages (MDMs). MDMs derived from 2 HIV-seronegative donors were infected with HIV-$1_{SF162}$, and then cultured in the presence of RV and ddI. Virus production was assayed on days 7 and 16 after infection and compared to that obtained in the infected MDMs not exposed to drugs. Data are that of FIG. 4 expressed as p24 antigen (ng/ml) and including control values. For each donor, values represent the mean±SD of three replicate infections. Diagonally-lined bars (///)—day 7; open bars—day 16.

For the present example, cultures were maintained in the presence of 10 μM RV and varying concentrations of ddI. The amount of p24 antigen produced in the supernatant was measured on days 7 and 16 after infection. Results from the 2 donors are displayed in FIG. 4 (virus production provided as % of untreated control) and in FIG. 17 (data provided as p24 antigen (ng/ml)). In the absence of ddI, RV at 10 μM exerted only a modest anti-HIV effect that varied between the 2 donors. However, a 10-fold or greater potentiation of ddI-antiviral activity was observed when the nucleoside analogue was combined with 10 μM RV.

In a separate study, MDMs cultured in the presence of 15 μM RV and 10 μM ddI for 5 weeks did not show signs of toxicity as measured by the MTT assay.

EXAMPLE 4

Suppression of Productive Infection in Resting Lymphocytes and Macrophages

The effect of RV and nucleoside analogues in infected resting T-lymphocytes was evaluated in the present example. Purified resting cells were used. Absence of activated lymphocytes in the preparation was determined by incubation of the cells in the presence of a monoclonal antibody directed against the low affinity IL-2 receptor CD25 (Pharmingen, San Diego, Calif.), and subsequent analysis by flow cytometry. Less than 5% resting cells were found to express the CD25 receptor. Cells were infected with HTLV-IIIB at a multiplicity of infection of $10^4$ $TCID_{50}/10^6$ cells for 3 hours. A high multiplicity of infection (m.o.i.) was used because of a reported short half life of HIV-1 unintegrated DNA in infected resting lymphocytes. Infected cells were washed 3 times with PBS to remove virus excess and resuspended in 10% FBS RPMI medium supplemented with drugs. To ensure that any antiviral activity exerted by the drugs occurred during the resting state, drugs were removed six days after infection by washing with PBS 3 times, and cells were activated by culturing in the presence of PHA for 2 days. Cells were then cultured in IL-2 medium without drugs, and supernatants were monitored for the presence of p24 antigen. Cultures were maintained for 20 days.

To further investigate the extent of viral inhibition, genomic DNA was extracted from cultured cells using QIAamp DNA blood kit (QIAGEN, Valencia, Calif.). PCR amplification was carried out in a 50 μl reaction containing 1 μg of DNA, HIV-1 primers SK 145/SK 431 (Innis et al., 1990, PCR Protocols, A Guide to Methods and Applications, 333–334), 0.25 mM dNTPs, 50 mM NaCl, 25 mM Tris-HCl, pH 8.0, 1.5 mM $MgCl_2$ and 2 units of Taq polymerase (Promega, Madison, Wis.). Thermocycling consisted of 4 min at 94° C. for one cycle, followed by 35 cycles (94° C., 30 seconds; 55° C., 1 min; 72° C., 1 min). Detection of amplified products was done following the liquid hybridization method using $^{32}$p end-labeled probe SK102 (Innis, ibid.). Hybridization products were separated in a 10% polyacrylaminde gel and detected by autoradiography. PCR standards were prepared by serially diluting crude lysates of the ACH-2 cell line, that carries one copy of HIV-1 genome per cell (Clouse, K., et al., 1989, J. Immunol. 142, 431–438), in DNA extracted from uninfected PBMC's. Presence of PCR inhibitors in the samples was assessed by amplification of a 242-bp region in the HLA-DQ-α locus (Saiki, R., et al., 1986, Nature 324, 163–166).

Figure 5:
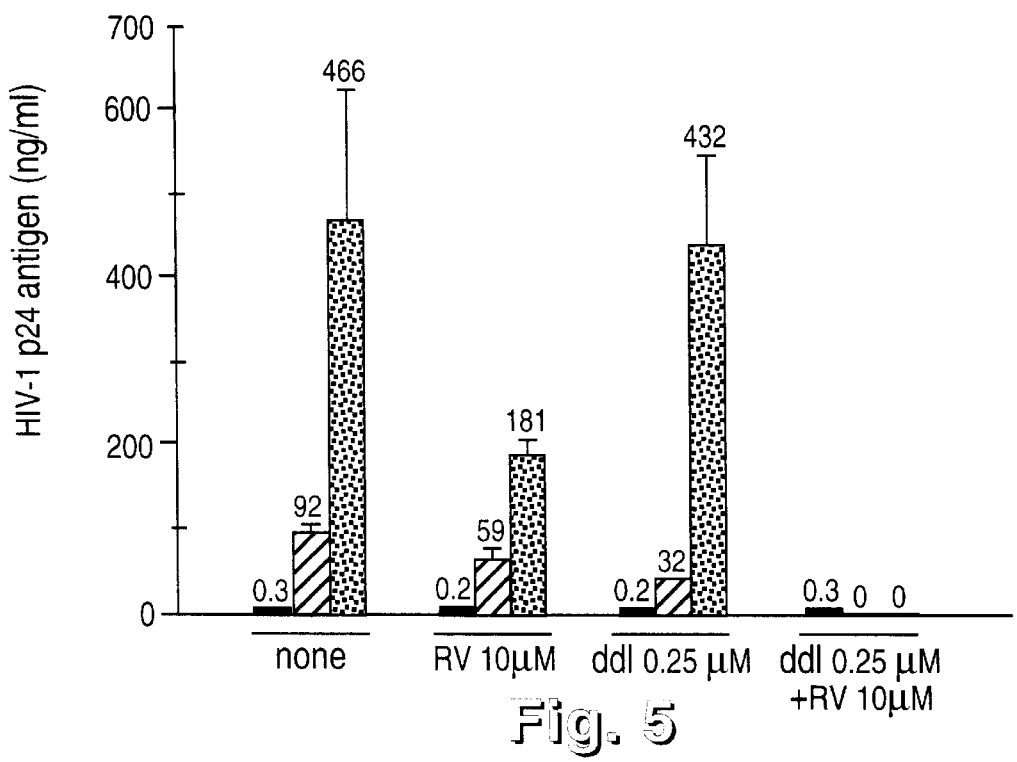
FIG. 5. Effect of RV and ddI on HTLV-IIIB infected resting T-lymphocytes that are exposed to drugs for 6 days preceding PHA activation. Resting T-lymphocytes were prepared as described in Example 4. Cells were infected and cultured in medium containing different drug combinations. On day 6 after infection, drugs were removed and cells activated. Viral p24 antigen was evaluated on days 14 and 20. Values represent the mean+/−S.D. of triplicate wells. Solid bars—day 6; diagonally-lined bars—day 14; dotted bars—day 20.
Figure 18:
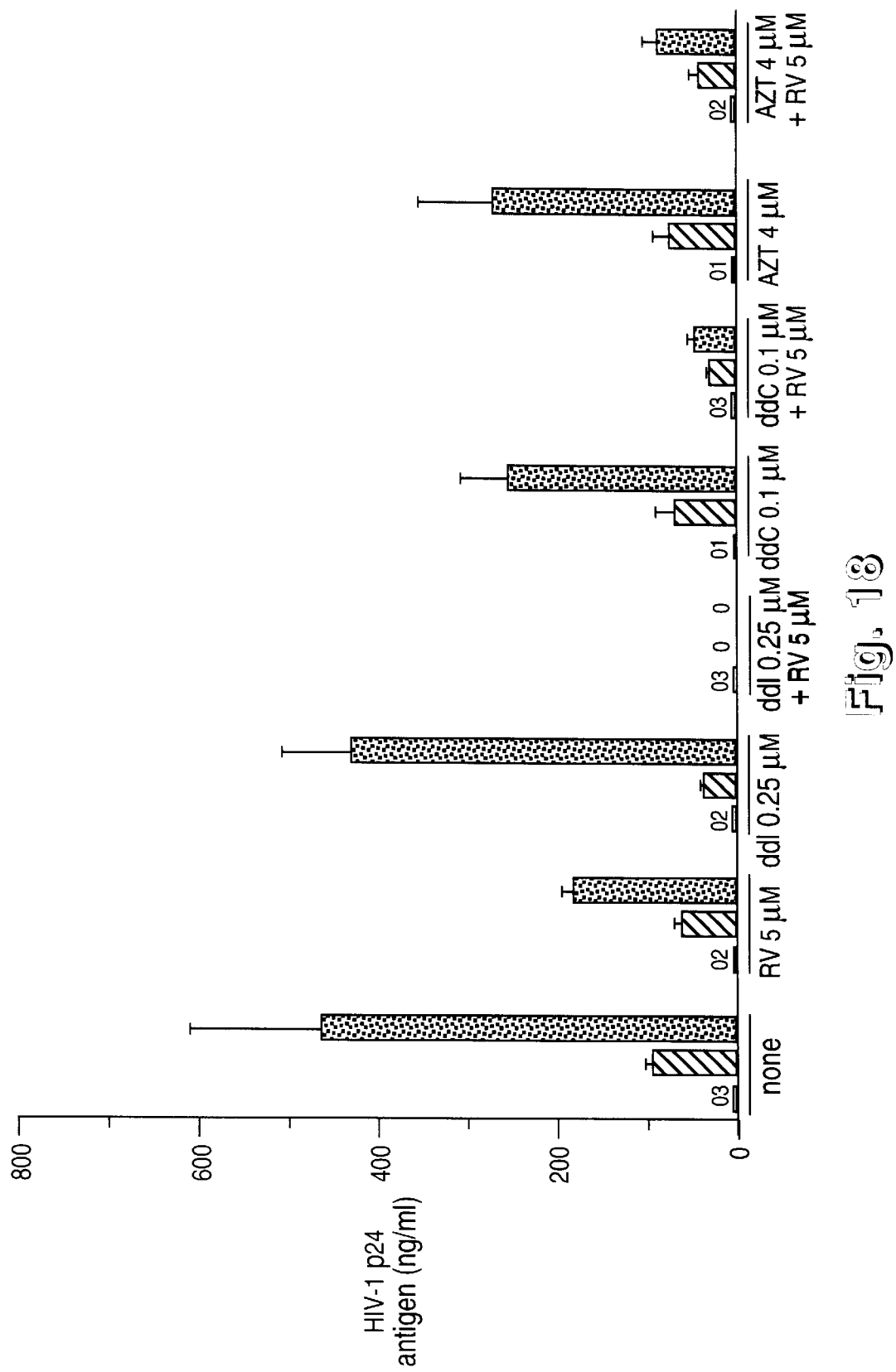
FIG. 18. Effect of RV and ddI, RV and ddC, and RV and AZT on HTLV-IIIB infected resting T-lymphocytes that are exposed to drugs for 6 days preceding PHA activation. Resting T-lymphocytes were prepared as described in Example 4. Cells were infected and cultured in medium containing different drug combinations. On day 6 after infection, drugs were removed and cells activated. Viral p24 antigen was evaluated on days 6, 14 and 20. The x-axis is drug presence prior to PHA activation. Values represent the mean±SD of three replicate infections. Open bars—day 6 (Levels are too low to show, numbered values are provided); diagonally-lined bars (///)—day 14; shaded bars—day 20.

Purified resting T-lymphocytes from a seronegative donor were infected with HTLV-IIIB at the high multiplicity of infection and cultured in the presence of 5 or 10 μM RV plus ddI (0, 0.25, 0.5 μM), ddC (0, 0.1 μM) or AZT (0, 4 μM) for 6 days. Concentrations used for ddC and AZT correspond to the highest, nontoxic concentration attainable in plasma of treated individuals. Low concentrations of ddI were used because previous studies demonstrated that concentrations of 1 μM were able to completely suppress virus production under these conditions. On day 6 after infection, drugs were washed away and cells were activated with PHA. The extent of viral replication was evaluated on day 6 (prior to PHA activation) and days 14 and 20 after infection. Results are presented in FIG. 5 and FIG. 18. On day 6 very low amounts of p24 antigen could be detected under every condition tested, likely representing residual virus from the infecting inoculum. On days 14 and 20, considerable virus production was detected following PHA activation in the drug-free culture as well as in the cultures containing either RV or nucleoside analog alone. However, no p24 antigen could be detected on days 14 or 20 in the cultures that had been treated with 5 or 10 μM RV plus 0.25 μM ddI. A similar result was obtained when 0.5 μM ddI was combined with 5 or 10 μM RV. DdI by itself did not suppress viral replication, however, no virus antigen could be detected in the cultures combining ddI and RV on days 14 or 20. No toxicity was found by the MTT assay in uninfected culture controls treated with 5 μM RV and 0.5 μM ddI for 20 days under the same conditions.

Figure 19:
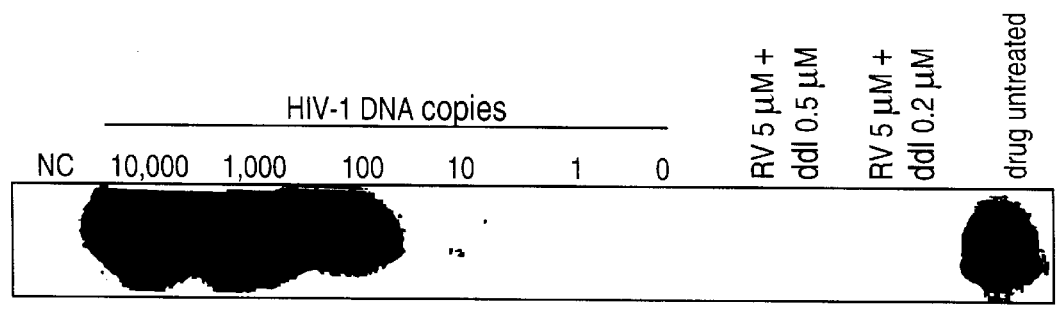
FIG. 19. HIV-1 PCR analysis of DNA extracted from cultured cells showing no p24 antigen production on day 20 after infection (cultures exposed to 5 $\mu$M RV plus 0.5- or 0.25 $\mu$M ddI). The drug-untreated sample corresponds to DNA extracted from cells cultured in the absence of drugs. Standards correspond to serial dilutions of the ACH-2 cell line, that harbors one copy of HIV-1 DNA per cell. NC is a PCR negative control. Similar PCR negative results were obtained with DNA extracted from cultured cells of a second donor.

Approximately 1 μg of DNA extracted from cultures yielding p24-negative values on day 20 was amplified by PCR using HIV-1 primers SK145/SK431 and probe SK 102. The system allows the detection of 10 HIV-1 proviral DNA copies in a background of 1 μg of cellular DNA. However, amplification of DNA extracted from cultures exposed to 5 μM RV and 0.25- or 0.5 μM ddI yielded negative PCR signals. In contrast, the drug-untreated control yielded a strong amplification signal (FIG. 19). Amplification of the same samples with HLA-DQ primers indicated absence of PCR inhibitors. In the case of ddC and AZT, the combinations with RV resulted in a reduction of virus antigen productions when compared to the nucleoside analogs alone, but failed to suppress virus replication.

In a separate study designed to assess cell viability, uninfected cells were cultured under the same conditions in the presence or absence of drugs. No difference in viability was found after being cultured for 20 days.

These results demonstrate that combinations of 5 or 10 μM RV and low concentrations of ddI are able to inhibit the establishment of a productive HIV-1 infection in resting T-lymphocytes. Any virus present after treatment and activation appears to be replication-incompetent. This near complete inhibition of HIV replication was demonstrated in a resting cell model of infected cells prior to activation. The results also demonstrate that RV potentiates the anti-HIV activity of AZT and ddC in resting lymphocytes. Therefore, from these data, one of skill in the art would expect that combination compositions as provided herein would provide for inhibition of a productive infection in infected individuals.

Figure 6:
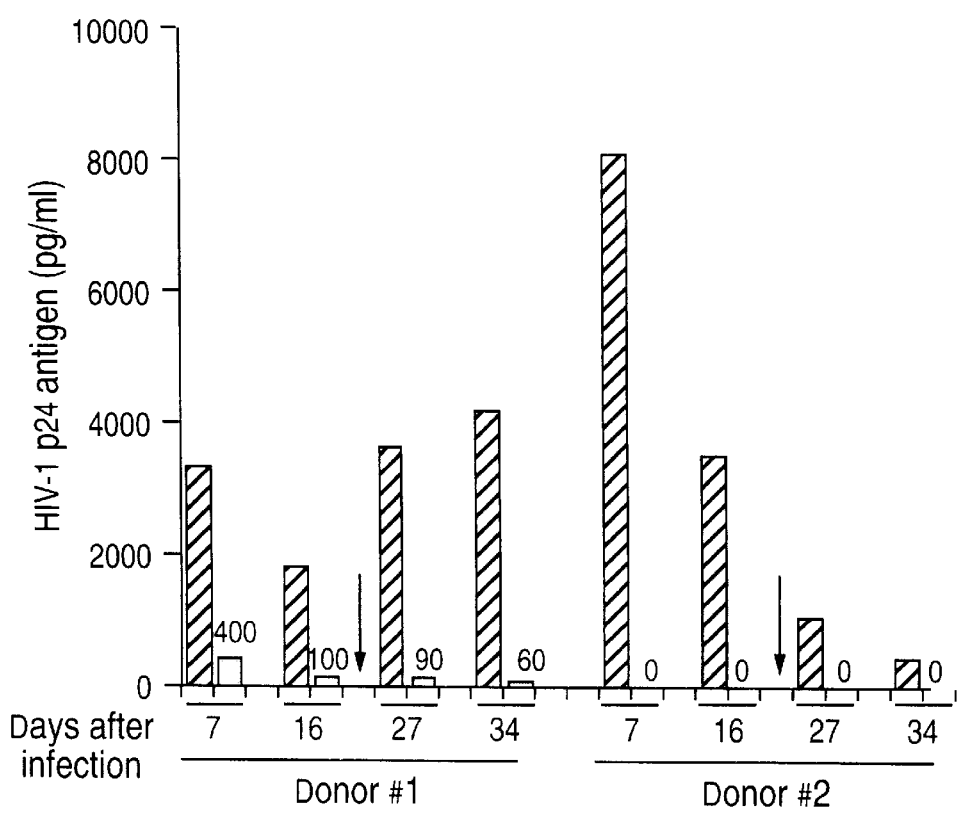
FIG. 6. Effect of drug suspension on HIV-1$_{SF162}$ infected macrophages. Infected macrophages were monitored for p24 antigen production on days 7 and 16 after infection. Drugs were removed on day 20 (vertical arrows), and cultures maintained for an additional 14 days. Diagonally-lined bars—ddI, 10 $\mu$M; open bars—ddI, 10 $\mu$M+resveratrol, 10 $\mu$M.

Having demonstrated that RV potentiates the antiviral effect of ddI in infected MDM's (Example 3), a study was carried out to evaluate whether high concentrations of ddI could completely suppress virus replication in MDM's when added in combination with RV. MDMs derived from 2 seronegative donors were infected with the SF 162 strain of HIV-1 and cultured in the presence of 10 μM ddI, a plasma level attainable in treated individuals. The anti-HIV effect of this concentration of ddI was investigated in the presence or absence of 10 µM RV. DdI alone (10 µM) inhibited viral replication by more than 90% in both donors on day 7 after infection. However, the culture containing 10 µM RV plus 10 µM ddI completely suppressed virus production in macrophages from donor #2 on days 7 and 16 after infection, and by 99.8% in the macrophages of donor #1 as shown in FIG. 6. The strong antiviral activity achieved by RV plus ddI on day 16 was further analyzed by removing the drugs from the culture. The drugs were then removed on day 20 and the macrophages maintained in culture for an additional 14 days. In donor #1 MDMs, a virus rebound followed drug removal in the cultures that had been exposed to ddI alone. However, there was minimal virus being produced in the RV plus ddI treated cultures. In donor #2 MDMs, drug removal did not result in viral rebound. However, the ddI-only treated cultures continued releasing virus while the ddI plus RV-treated cultures remained negative for p24 antigen production.

These results indicate that RV potentiates the activity of ddI in macrophages. At a concentration of ddI equivalent to an attainable in vivo concentration (10 µM), the ddI/RV combination was able to completely suppress viral replication in one of the tested donors (donor #2), and strongly inhibited replication in the other donor (donor #1). Interestingly, the donor cells (donor #2) that did not release virus in the presence of RV and ddI, failed to do so even when the drugs were removed from the medium. The viability of MDMs was not affected by concentrations of up to 15 µM RV and 10 µM ddI in the culture.

EXAMPLE 5

Resveratrol is as Effective as Hydroxyurea at a Dose 10-Fold Lower than that of HU RV and hydroxyurea (HU) were compared for their enhancement of antiviral activity of ddI. Hydroxyurea was purchased from Sigma (St. Louis, Mo.).

Figure 7:
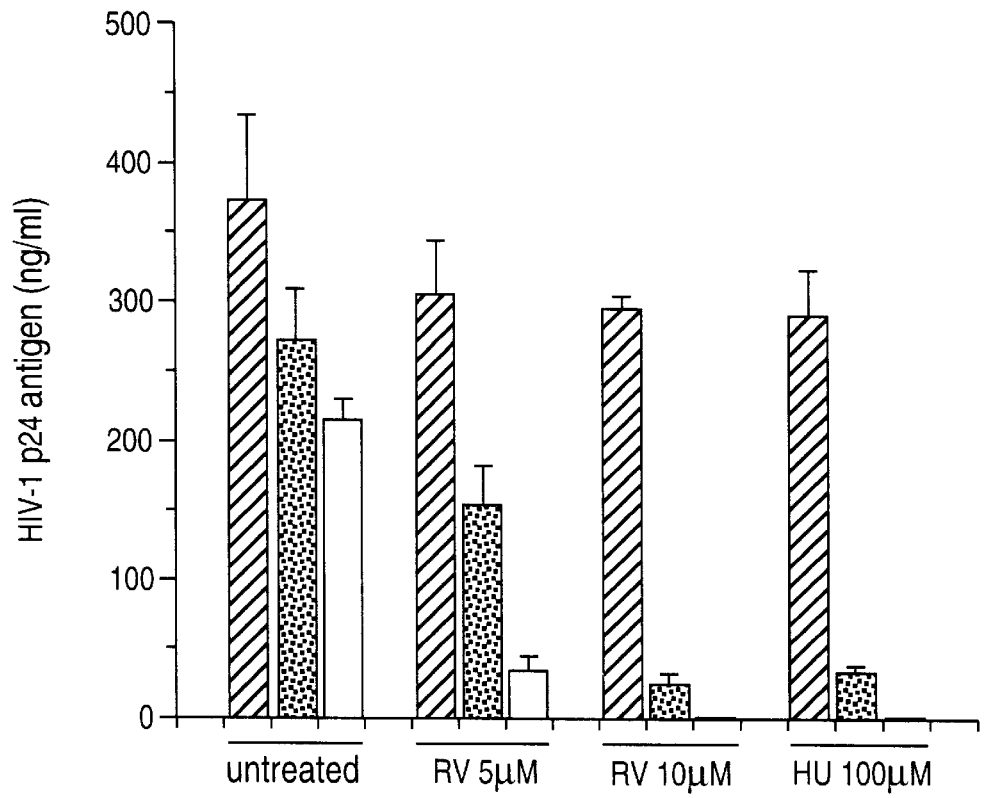
FIG. 7. Comparison of ddI-antiviral enhanced activity with HU or RV. Activated PBMCs were infected with HTLV-IIIB and cultured in the presence of ddI and RV or HU at the listed concentrations. Data indicates p24 antigen values of the supernatants on day 7 post infection. Each data point represents the mean+/−SD of triplicate wells. Diagonally-lined bars—no ddI; dotted bars—ddI, 0.25 $\mu$M; open bars—ddI, 0.5 $\mu$M.

Activated PBMCs infected with HTLV-IIIB were cultured in the presence of ddI plus HU (100 µM) or RV (5 and 10 µM). HU was used at 100 µM because at this concentration HU potently synergizes with ddI in inhibiting HIV-1 replication without causing cellular toxicity (Lori, et al., Science 266:801–805, 1994). Higher concentrations of HU have been shown to promote cell death (Yoshioka, et al., J. Biol. Chem., 262:8235–8241, 1987). Virus production in the presence of the different drug concentrations was evaluated on day 7 after infection. Data are provided in FIG. 7. RV at 10 µM and HU at 100 µM reduced virus production by approximately 20% when used alone, compared to the untreated control. RV and HU, each in combination with ddI, both exerted a similar anti-HIV effect in activated PBMC's. In combination with 0.25 µM ddI, 10 µM RV and 100 µM HU inhibited HIV-1 replication by 94 and 91%, respectively. When combined with 0.5 µM ddI, both drugs inhibited virus replication by more than 99%.

These data demonstrate that RV plus ddI would be expected to be a more potent combination in vivo than HU plus ddI since 10-fold less RV demonstrated similar anti-HIV activity when combined with ddI as compared to the HU-ddI combination.

EXAMPLE 6

Effects of Resveratrol and Hydroxyurea on Cell Proliferation

The effect of RV and IU on PBMC proliferation at the concentrations shown to enhance the anti-HIV effect of ddI were examined. Cellular proliferation in culture in the presence or absence of drugs was measured by commercial MTT assay, according to the manufacturer's instructions (Boehringer Mannheim). Cell viability was determined by trypan blue staining.

Figure 8:
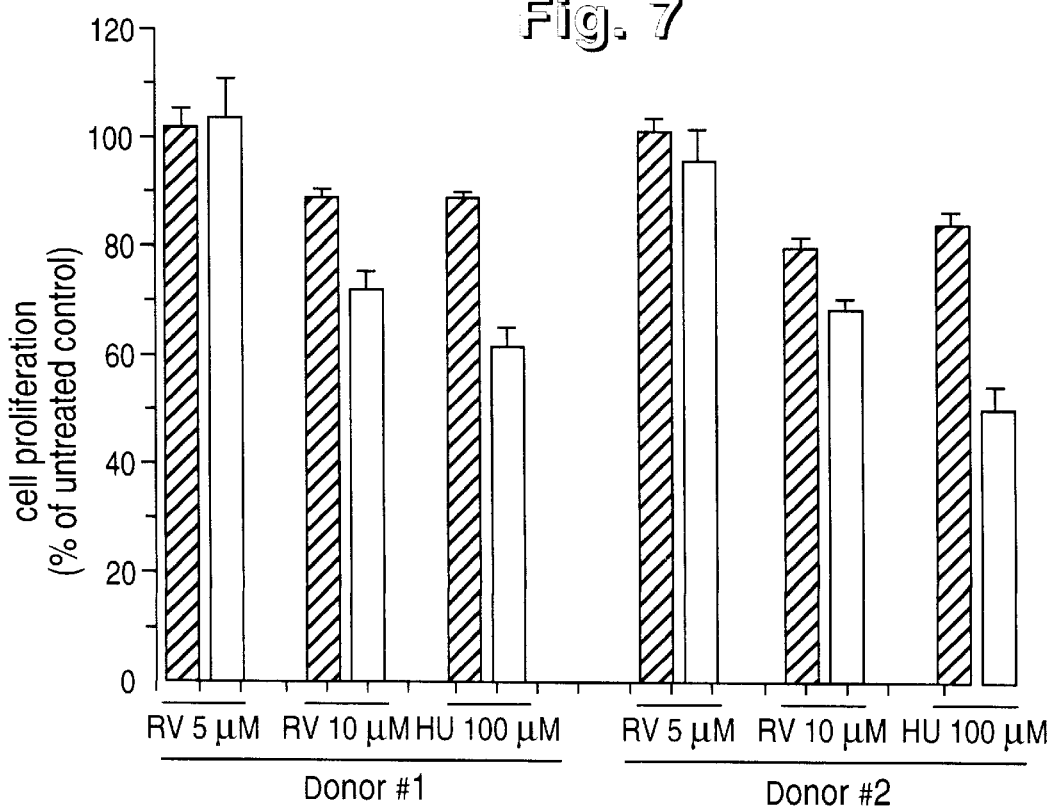
FIG. 8. Antiproliferative activity resulting from adding RV or HU to PHA-activated PBMCs cultured in the presence of IL-2 and 2 $\mu$M ddI. Uninfected cells were cultured in the presence of drugs and an MTT assay was performed on days 2 and 5. Cell number is indicated as % of cells as compared to the untreated PBMC control. Diagonally-lined bars—day 2; open bars—day 5.
Figure 20:
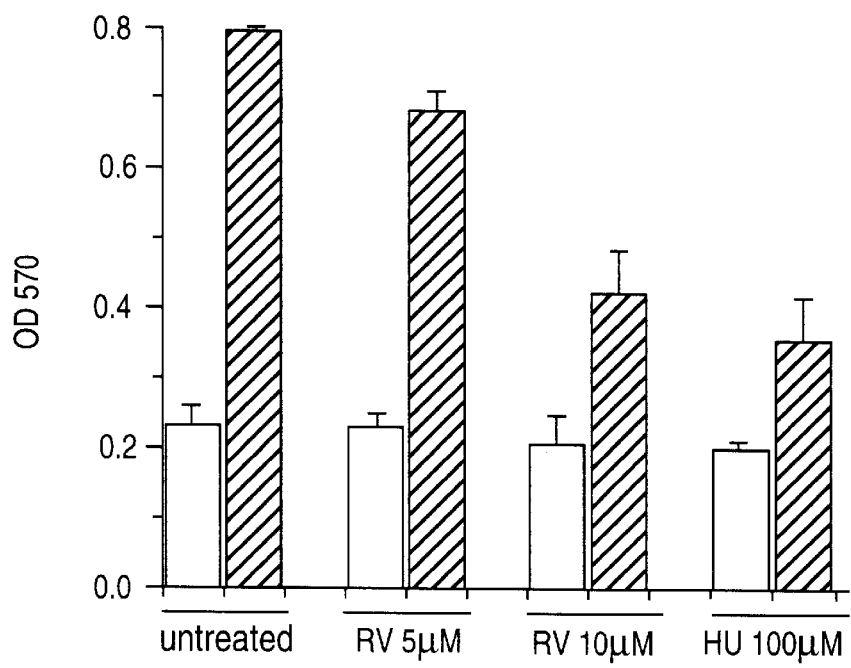
FIG. 20. Antiproliferative activity resulting from adding RV or HU to PHA-activated PBMCs cultured in the presence of IL-2 and 2 $\mu$M ddI. Uninfected cells were cultured in the presence of drugs and an MTT assay was performed on days 2 and 7. Data are provided as OD at 570 nm (mean±SD from three donors). Background OD values were less than 0.03. Open bars—day 2; diagonally-lined bars (///)—day 7.

Proliferation was measured on PHA-stimulated PBMCs cultured in the presence of IL-2, 2 µM ddI, and RV or HU. The MTT assay was performed on days 2 and 5 (FIG. 8), and days 2 and 7 (FIG. 20) after the addition of the drugs. Minimal impact on cell proliferation was seen with 5 µM RV, a concentration that resulted in significant suppression of viral replication when combined with ddI (FIG. 1 and 14–16). On day 2, both RV 10 µM and HU inhibited proliferation slightly. On day 5, RV at 10 µM inhibited proliferation by 30%, whereas HU inhibited proliferation by 40 to 50%, depending on the donor. On day 7, the OD values obtained in the MTT assay for cultures containing 10 µM RV were higher than those obtained with 100 µM HU, therefore suggesting a lesser antiproliferative effect.

In a separate study designed to assess cell viability by trypan blue staining, PHA-activated PBMCs were cultured for 7 days in the presence of IL-2, 2 µM ddI, plus varying concentrations of RV. When RV was used at 25 µM, over 60% of cells became trypan blue stained, therefore indicating cell death. In the absence of RV or when RV was used at 5 or 10 µM, values of more than 95% cell viability were obtained.

There is reasonable concern regarding the use of cellular antiproliferative agents in the treatment of HIV-1 disease. The data provided herein indicate that RV enhances the anti-HIV activity of nucleoside analogs, especially ddI, at 5 µM, a concentration with no antiproliferative effects. At 10 µM RV there was only a slight antiproliferative effect, somewhat less than that observed with 100 µM HU. The difference in antiproliferative activity may have important clinical implications, since a limiting factor for usage of HU is its antiproliferative, bone marrow suppressive effects. The present results also demonstrate that a combination of RV plus ddI may also offer a more favorable toxicity profile.

EXAMPLE 7

Inhibition of Nucleoside Analog-Resistant Isolates by Resveratrol and ddI

The present example provides data to test whether viral isolates carrying mutations in the RT gene that confer resistance to ddI could be rendered sensitive when the nucleoside analogue was combined with RV. Viruses containing one or more of the mutations associated with resistance to ddI, e.g., an isolate carrying the L74V mutation which confers primary resistance to ddI, a virus isolate carrying 4 different resistance-associated mutations in the RT gene (HIV-1 RTMDR1) were used to infect PHA-stimulated PBMCs. The HIV-$1_{74V}$ isolate, and the HIV-$1_{RTMDR1}$ isolate (containing the M41L, L74V, V106A and T215Y mutations, conferring resistance to AZT, ddI, nevirapine and other non-nucleotide RT inhibitors) were obtained from Dr. Larder at the National Institutes of Health AIDS Research and Reference Reagent Program (Catalog #2528 and #2529, respectively, Rockville, Md.). In addition, viruses having mutations 65R, 74V, 184V in the RT gene, and a virus containing the multiple-nucleoside-resistance mutation 151M were assayed in infectivity assays using RV plus ddI. The mutations present in the RT gene of each virus as well as their susceptibility to ddI are as follows: HIV-$1_{74V}$(ddI$_{IC90}$=2.6 µM); HIV-$1_{41L, 74V, 106A, 215Y}$(ddI$_{IC90}$=4.5

μM); HIV-1$_{65R, 74V, 184V}$ (ddI$_{IC90}$>20 μM) and HIV-1$_{62V, 751, 77L, 151M}$ (ddI$_{IC90}$>20 μM).

Figure 9:
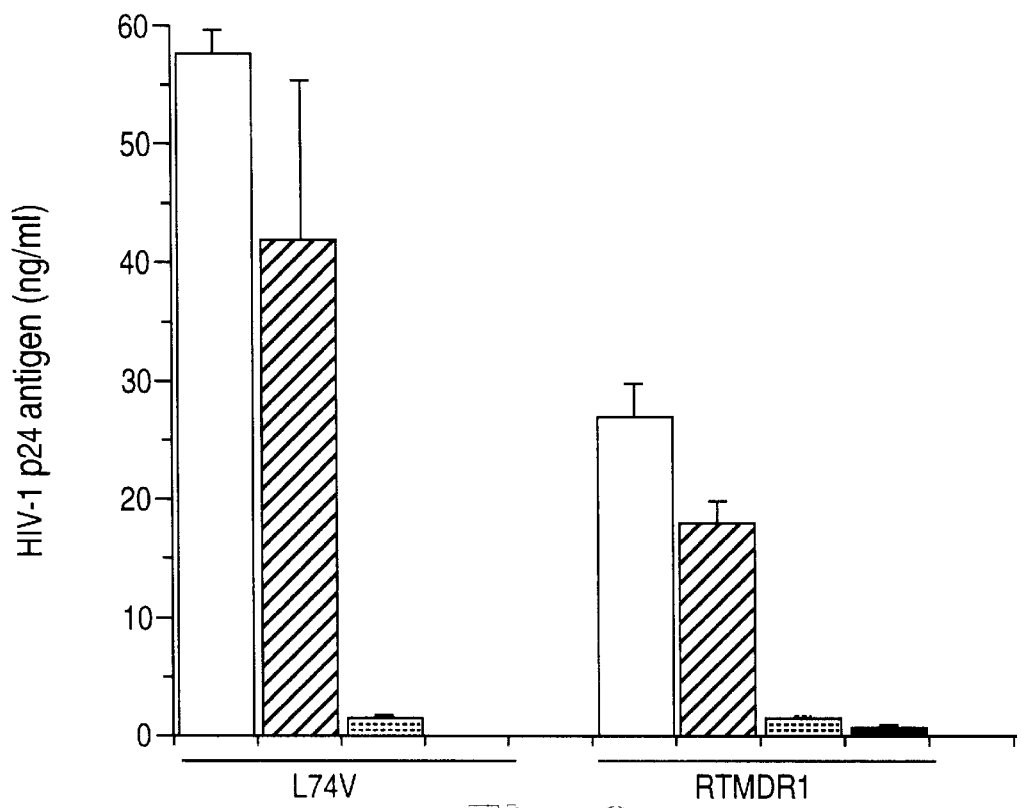
FIG. 9. Inhibition of drug-resistant HIV-1 isolates by RV and ddI. An isolate containing the ddI-conferring-resistance L74V mutation in the RT gene, and the isolate RTMDR1 that contains 4 mutations conferring resistance to several nucleoside analogs were used in infection assays involving activated PBMCs. Values indicate the amount of p24 antigen released in the supernatant. Values are the mean+/–S.D. of duplicate wells. Open bars—no drug; diagonally-lined bars—ddI, 2 $\mu$M; shaded bars—ddI, 2 $\mu$M+resveratrol 5 $\mu$M; solid bars—ddI, 2 $\mu$M+resveratrol 10 $\mu$M.
Figure 21:
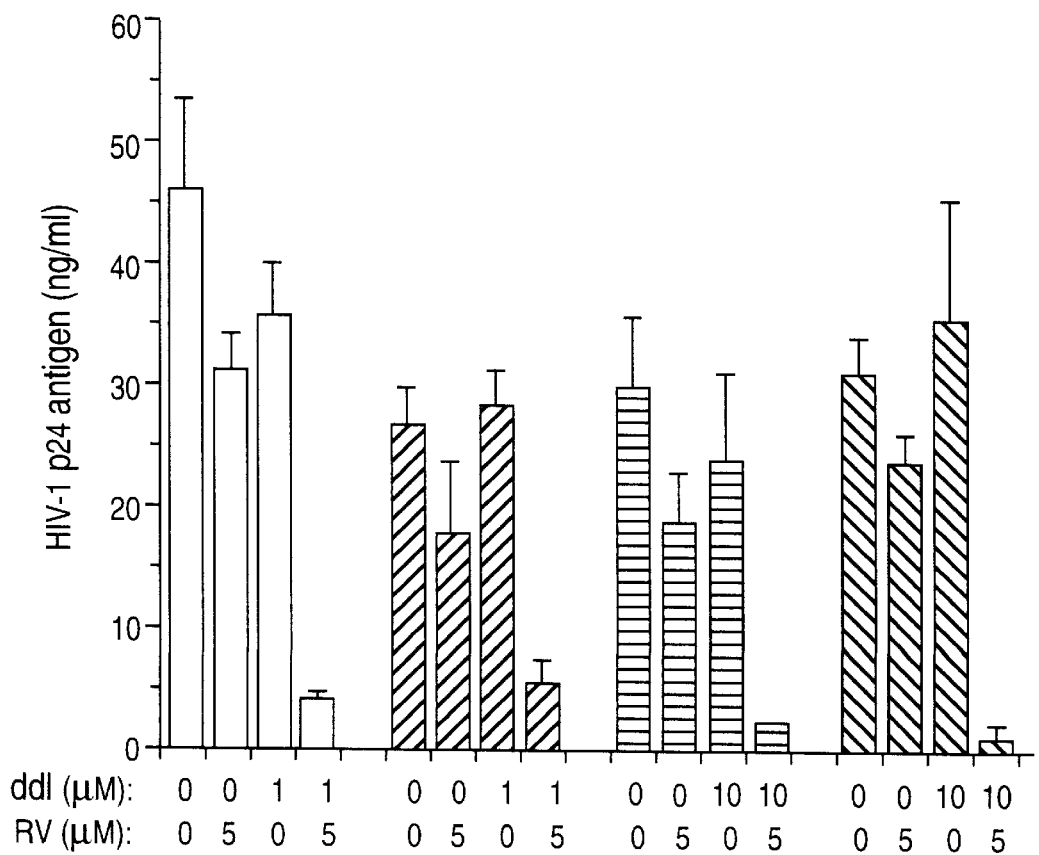
FIG. 21. Inhibition of drug-resistant HIV-1 isolates by RV and ddI. An isolate containing the ddI-conferring-resistance L74V mutation in the RT gene, and three RT-multidrug-resistant isolates were used in infection assays involving activated PBMCs. Values indicate the amount of p24 antigen released in the supernatant and are the mean±SD of three replicate infections. Open bars—74V; diagonally-lined bars (///)—41L, 74V, 106A, 215Y; horizontally-lined bars—65R, 74V, 184V; diagonally-lined bars (///)—62V, 75I, 77L, 151M.

Infected cells were cultured in the presence of 2 μM ddI with and without RV (FIG. 9) and in the presence of 5 μM RV and various concentrations of ddI (FIG. 21). With 2 μM ddI, a modest suppression of viral replication was observed for both viral isolates—28% suppression in the isolate with the L74V mutation, and 34% suppression in the RTMDR1 isolate. However, in the presence of 5 μM RV and 2 μM ddI there was a greater than 95% viral suppression of both resistant isolates. When 2 μM ddI was added to 10 μM RV, greater than 98% inhibition of viral replication was achieved. As shown in FIG. 21, at concentrations at which ddI exerted slight or no antiviral activity, the combination of RV and ddI decreased virus production by more than 80% as compared to ddI alone in all 4 isolates.

These data demonstrate that the combination of RV and ddI is able to restore the phenotypic resistance of RT-multidrug-resistant variants of HIV-1 to ddI. A combination as provided by the present invention is expected to be useful in the physician's armamentarium against retroviral infections, and especially useful in providing further options beyond current protocols.

EXAMPLE 8

RV Promotes DNA Synthesis while HU inhibits DNA Synthesis

The present study demonstrates that resveratrol promotes DNA synthesis while, in contrast, hydroxyurea is demonstrated to inhibit DNA synthesis.

Figure 10:
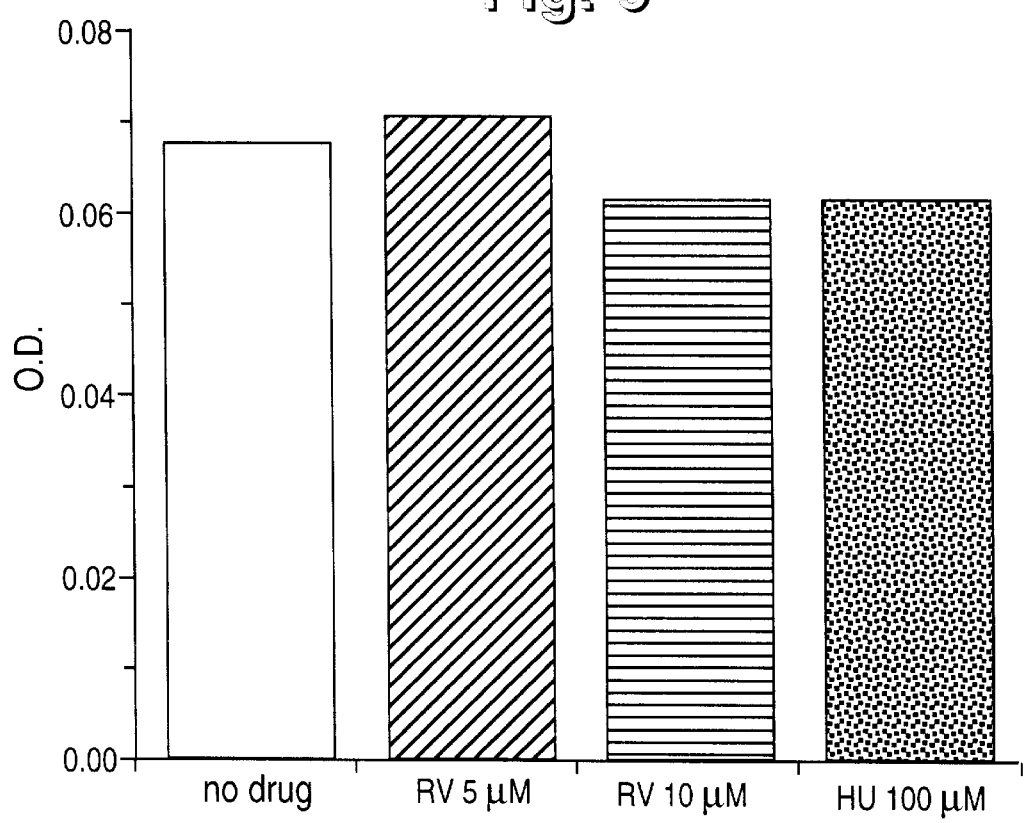
FIG. 10. Effect of RV and HU on cell proliferation. PHA-activated PBMCs from a seronegative donor cultured in the presence of IL-2 (10 units/ml) and drugs at the indicated concentrations. An MTT assay was performed on day 2. Data are the mean of triplicate wells.
Figure 11:
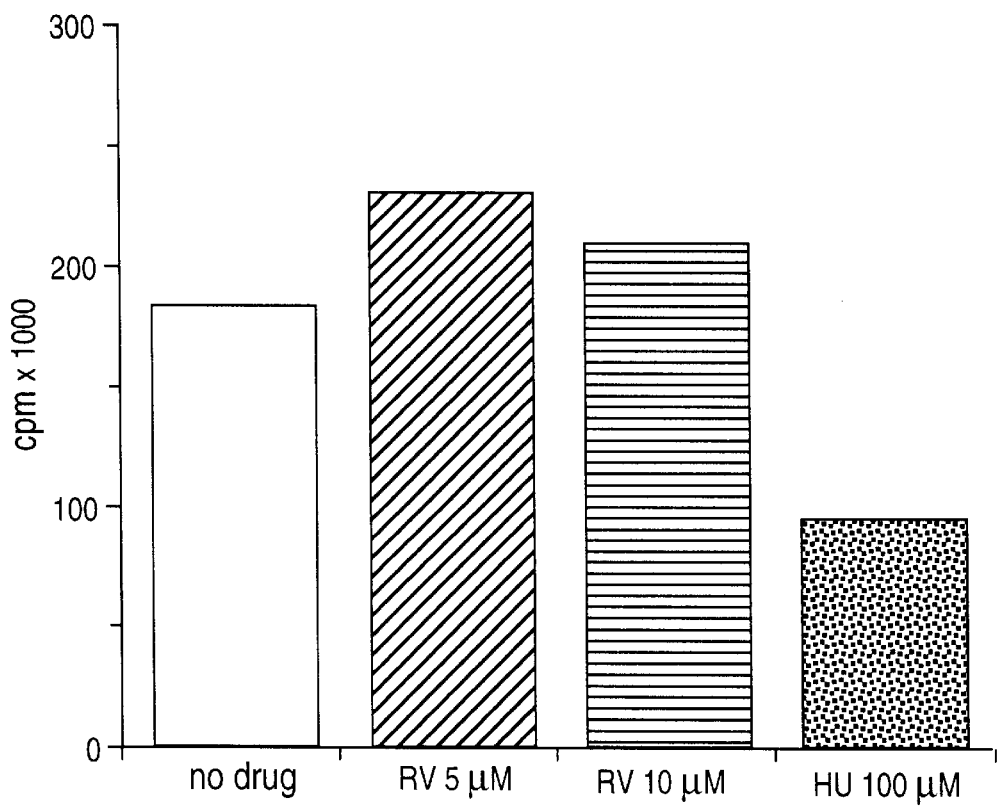
FIG. 11 Effect of RV and HU on cellular DNA synthesis. PHA-activated PBMCs from a seronegative donor cultured in the presence of IL-2 (10 units/ml) and drugs at the indicated concentrations. DNA synthesis was assayed by measuring the amount of radioactive thymidine incorporated on day 2. Data are the mean of triplicate wells.
Figure 12:
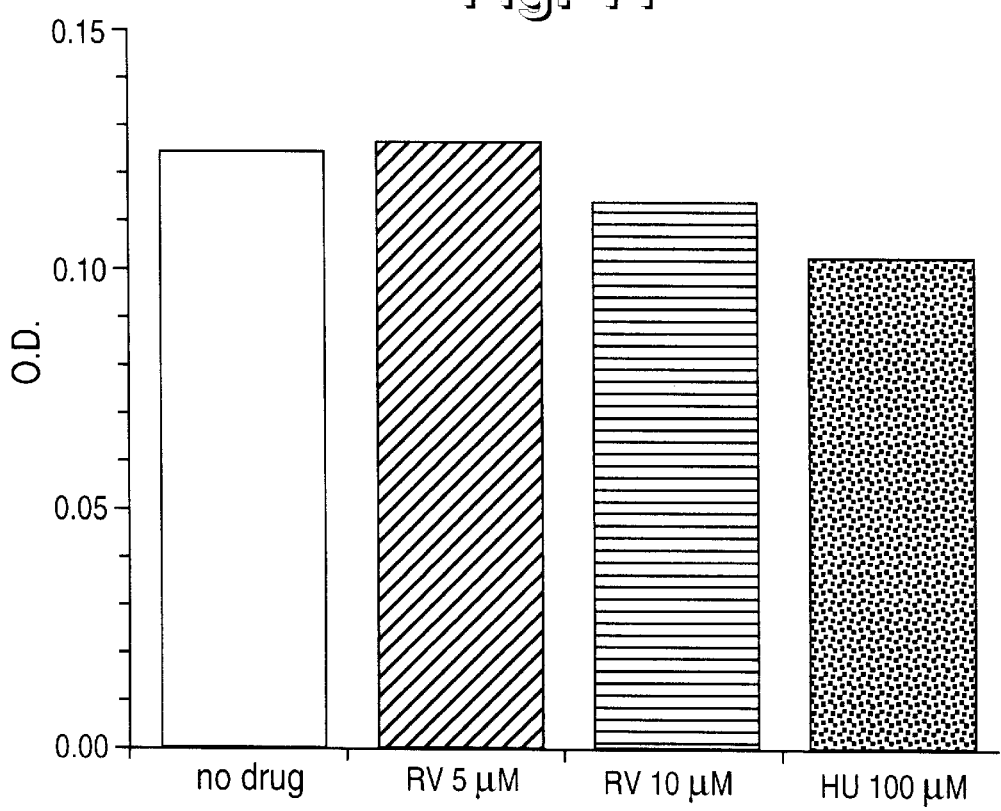
FIG. 12 Effect of RV and HU on cell proliferation. PHA-activated PBMCs from a seronegative donor cultured in the presence of IL-2 (10 units/ml) and drugs at the indicated concentrations. An MTT assay was performed on day 5. Data are the mean of triplicate wells.
Figure 13:
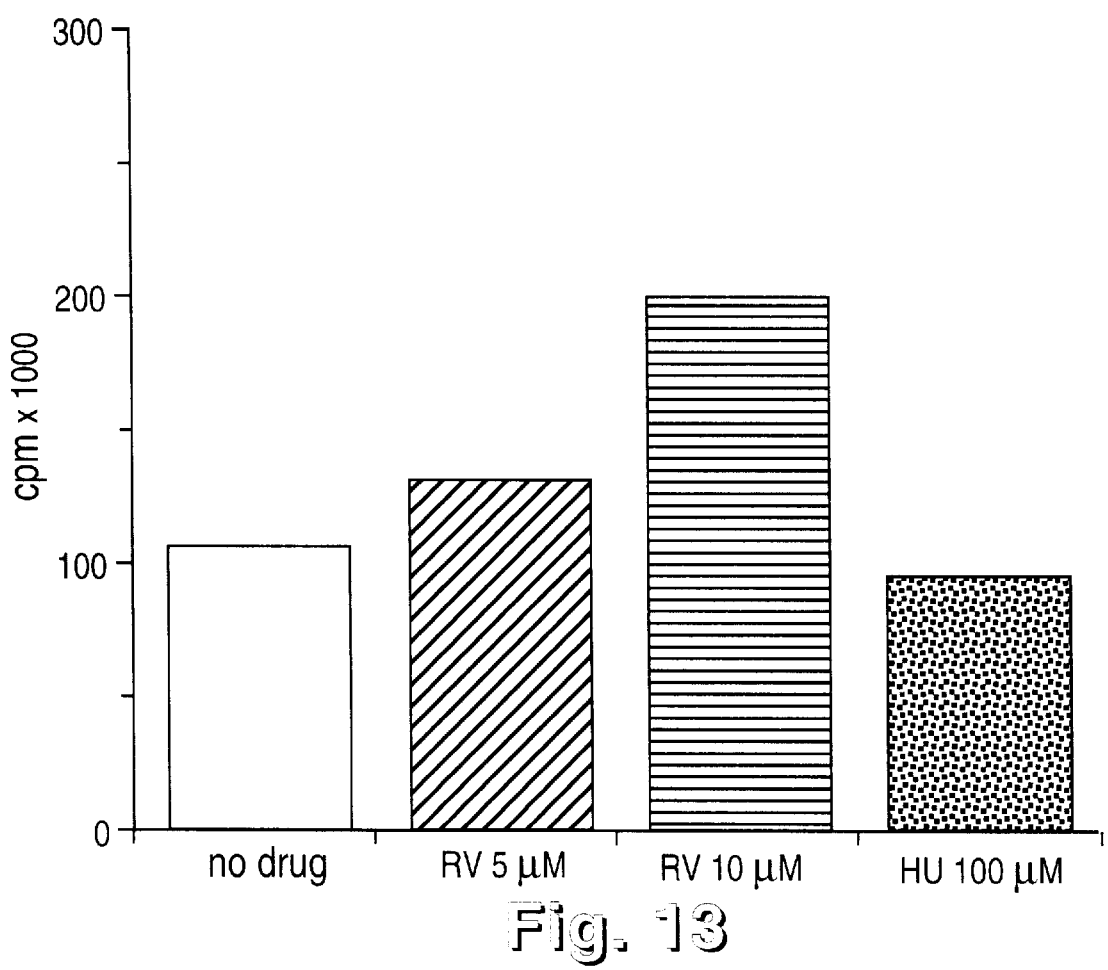
FIG. 13 Effect of RV and HU on cellular DNA synthesis. PHA-activated PBMCs from a seronegative donor cultured in the presence of IL-2 (10 units/ml) and drugs at the indicated concentrations. DNA synthesis was assayed by measuring the amount of radioactive thymidine incorporated on day 5. Data are the mean of triplicate wells.
Figure 14:
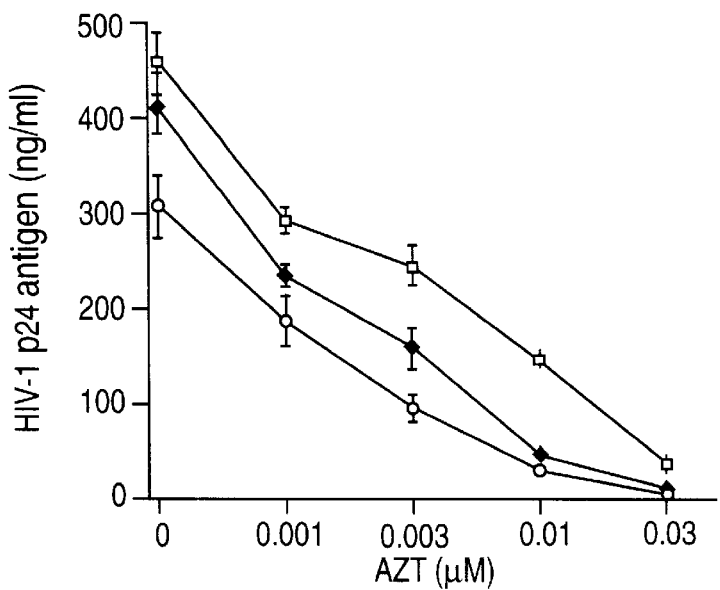
FIG. 14. Effect of RV in HIV-1 replication and its interaction with AZT. PHA-activated PBMCs were infected with HTLV-IIIB and cultured in the presence of varying concentrations of RV with and without AZT. HIV-1 replication was measured as p24 antigen in the culture supernatants on days 7 and 10 after infection. Peak virus production occurred on day 7 and p24 values are shown. Data represent mean±SD for three donors, with triplicate determinations in the study. Open squares—no RV; closed diamonds—RV, 5 $\mu$M; open circles—RV, 10 $\mu$M.
Figure 15:
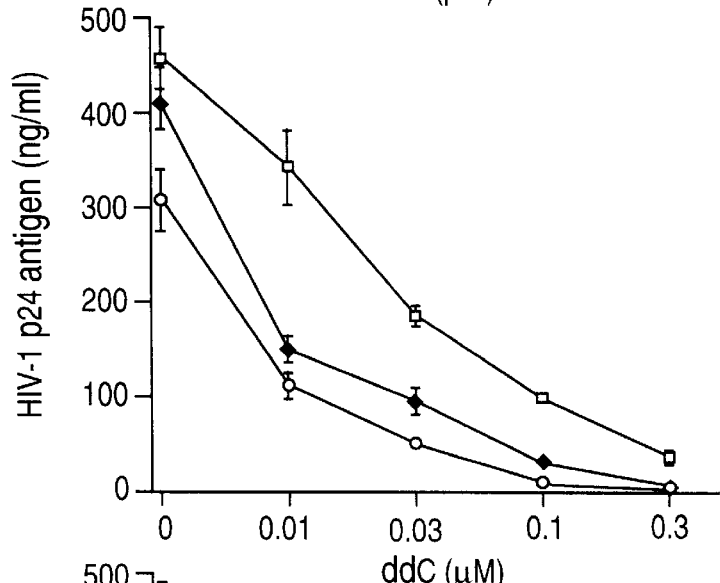
FIG. 15. Effect of RV in HIV-1 replication and its interaction with ddC. PHA-activated PBMCs were infected with HTLV-IIIB and cultured in the presence of varying concentrations of RV with and without ddC. HIV-1 replication was measured as p24 antigen in the culture supernatants on days 7 and 10 after infection. Peak virus production occurred on day 7 and p24 values are shown. Data represent mean±SD for three donors, with triplicate determinations in the study. Open squares—no RV; closed diamonds—RV, 5 $\mu$M; open circles—RV, 10 $\mu$M.
Figure 16:
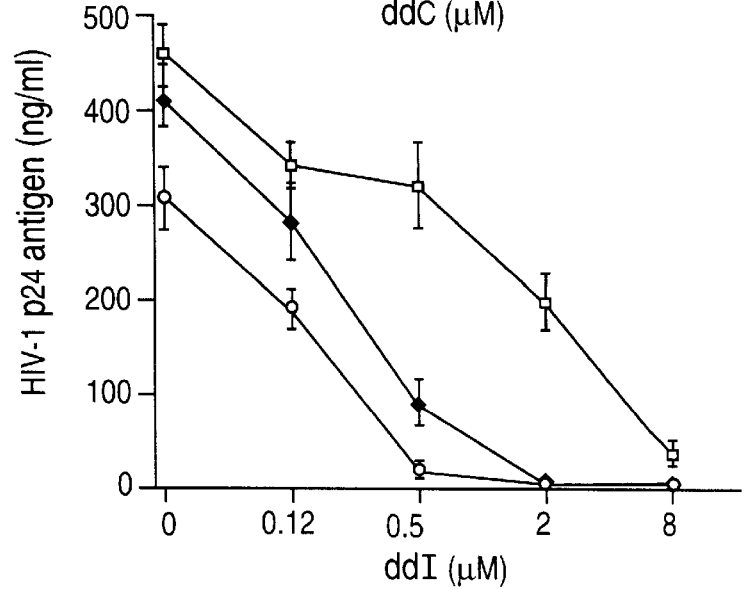
FIG. 16. Effect of RV in HIV-1 replication and its interaction with ddI. PHA-activated PBMCs were infected with HTLV-IIIB and cultured in the presence of varying concentrations of RV with and without ddI. HIV-1 replication was measured as p24 antigen in the culture supernatants on days 7 and 10 after infection. Peak virus production occurred on day 7 and p24 values are shown. Data represent mean+SD for three donors, with triplicate determinations in the study. Open squares—no RV; closed diamonds—RV, 5 $\mu$M; open circles—RV, 10 $\mu$M.

Proliferating PBMCs were cultured in the presence of RV or HU for 5 days. On day 2 and 5 an MTT assay and a $^3$H-thymidine incorporation assay were performed. The MTT is a calorimetric assay that measures cellular metabolic activity and directly correlates to the number of cells in the culture. The $^3$H-thymidine incorporation assay relies on the incorporation of the radioactive nucleoside $^3$H-thymidine into newly synthesized DNA. The data of FIG. 10 show that RV (10 μM) and HU (100 μM) treated cells yielded identical MTT values that were slightly lower than the untreated control. However, when $^3$H-thymidine incorporation is measured (FIG. 11), the HU-treated culture yielded results much lower than the untreated control, demonstrating an inhibition of DNA synthesis. In contrast, the RV-treated cultures showed higher amounts of $^3$H-thymidine incorporation than the untreated control, demonstrating increased DNA synthesis. Taken together, these data demonstrate that RV (10 μM) and HU (100 μM) exert dramatically different effects on DNA synthesis. These differences between the effects of RV and HU were even more striking in the MTT and $^3$H-thymidine incorporation assays conducted on day 5 (FIG. 12 and FIG. 13, respectively).

Genomic DNA was extracted from cultured cells using QIAamp DNA blood kit (QIAGEN, Valencia, Calif.). PCR amplification was carried out in a 50 μl reaction containing 1 μg of DNA, HIV-1 primers SK 145/SK 431 (Innis et al., 1990, PCR Protocols, A Guide to Methods and Applications, 333–334), 0.25 mM dNTPs, 50 mM NaCl, 25 mM Tris-HCl, pH 8.0, 1.5 mM MgCl$_2$ and 2 units of Taq polymerase (Promega, Madison, Wis.). Thermocycling consisted of 4 min at 94° C. for one cycle, followed by 35 cycles (94° C., 30 seconds; 55° C., 1 min; 72° C., 1 min). Detection of amplified products was done following the liquid hybridization method using $^{32}$p end-labeled probe SK102 (Innis, ibid.). Hybridization products were separated in a 10% polyacrylaminde gel and detected by autoradiography. PCR standards were prepared by serially diluting crude lysates of the ACH-2 cell line, that carries one copy of HIV-1 genome per cell (Clouse, K., et al., 1989, J. Immunol. 142, 431–438), in DNA extracted from uninfected PBMC's. Presence of PCR inhibitors in the samples was assessed by amplification of a 242-bp region in the HLA-DQ-α locus (Saiki, R., et al., 1986, Nature 324, 163–166).

All of the compositions and methods disclosed and claimed herein can be made and executed without undue experimentation in light of the present disclosure. While the compositions and methods of this invention have been described in terms of preferred embodiments, similar substitutes and modifications apparent to those skilled in the art are deemed to be within the spirit, scope and concept of the invention as defined by the appended claims. Following long-standing patent law convention, the terms "a" and "an" mean "one or more" when used in this application, including the claims.

What is claimed is:

1. A method of treating a viral infection in a subject in need thereof, comprising: administering to the subject a combination of
   an agent that promotes DNA synthesis in a virally-targeted cell, and
   a nucleoside analogue having antiviral activity.

2. The method of claim 1 wherein the viral infection is due to a retrovirus.

3. The method of claim 1 wherein the viral infection is due to a DNA virus.

4. The method of claim 1 wherein the treating is prophylactic.

5. The method of claim 1 wherein the treating is therapeutic.

6. The method of claim 1 wherein the agent that promotes DNA synthesis is a hydroxylated stilbene.

7. The method of claim 6 wherein the hydroxylated stilbene is a dihydroxystilbene.

8. The method of claim 6 wherein the hydroxylated stilbene is a trihydroxystilbene.

9. The method of claim 6 wherein the hydroxylated stilbene is a tetrahydroxystilbene.

10. The method of claim 1 wherein the virally-targeted cell is a CD4+T-lymphocyte.

11. The method of claim 10 wherein the CD4+T-lymphocyte is activated.

12. The method of claim 10 wherein the CD4+T-lymphocyte is resting.

13. The method of claim 1 wherein the virally-targeted cell is macrophage.

14. The method of claim 1 wherein the agent that promotes DNA synthesis is a trihydroxystilbene and the nucleoside analogue is a dideoxynucleoside.

15. The method of claim 1 wherein the combination has a weight ratio of agent to analogue of from 1:1 to 1:1,000.

16. The method of claim 1 wherein the combination has a weight ratio of analogue to agent of from 1:1 to 1:1,000.

17. The method of claim 1 wherein the subject is treatment experienced and has resistance to a nucleoside analogue.

18. The method of claim 1 wherein the subject is immune deficient.

19. The method of claim 1 wherein the subject is a perinatal subject.

20. The method of claim 14 wherein the trihydroxystilbene is resveratrol.

21. The method of claim 1 wherein the nucleoside analogue is dideoxyinosine, AZT, or dideoxycytosine.

22. The method of claim 1 further comprising the step of terminating the administering of the combination, thereby inducing a post-treatment period of viral incompetence.

23. A method of treating a viral infection in a subject in need thereof, comprising administering to the subject a combination of
   a hydroxylated stilbene that promotes DNA synthesis in a virally-targeted cell to yield an in vivo plasma concentration in the range of 1 $\mu$M–25 $\mu$M; and
   a nucleoside analogue having antiviral activity to yield an in vivo plasma concentration in the range of 0.01 $\mu$M–100 $\mu$M.

24. The method of claim 23 wherein the hydroxylated stilbene is resveratrol and the nucleoside analog is dideoxyinosine.

25. A method of treating a viral infection in a subject in need thereof, comprising: administering to the subject a combination of
   resveratrol to yield an in vivo plasma concentration in the range of 1 $\mu$M–25 $\mu$M; and
   dideoxyinosine to yield an in vivo plasma concentration in the range of 0.01 $\mu$M–100 $\mu$M.

26. A method of treating an immune deficient subject having a viral infection, comprising: administering to the subject a combination of
   a hydroxylated stilbene that promotes DNA synthesis in a virally-targeted cell, and
   a nucleoside analogue having antiviral activity.

27. A composition comprising
   a hydroxylated stilbene that promotes DNA synthesis in a virally-targeted cell, the stilbene in an amount so as to provide an in vivo plasma concentration of 1 $\mu$M–25 $\mu$M; and
   a nucleoside analogue having antiviral activity in an amount so as to provide an in vivo plasma concentration of 0.01 $\mu$M–100 $\mu$M when administered to a subject in need thereof.

28. The composition of claim 27 wherein the hydroxylated stilbene is resveratrol.

29. The composition of claim 27 wherein the nucleoside analogue is dideoxyinosine, AZT, or dideoxycytosine.

30. A unit dosage composition comprising 0.1 mg–1000 mg resveratrol and 0.05 mg–1000 mg dideoxyinosine.

31. A pharmaceutical kit for treatment of a viral infection in a subject in need thereof, the kit comprising in packaged combination:
   an agent that promotes DNA synthesis in a virally-targeted cell, and a nucleoside analogue having antiviral activity; and
   instruction for use in treating a viral infection.

* * * * *

UNITED STATES PATENT AND TRADEMARK OFFICE
CERTIFICATE OF CORRECTION

PATENT NO.    : 6,479,466 B1
DATED         : November 12, 2002
INVENTOR(S)   : Redfield et al.

It is certified that error appears in the above-identified patent and that said Letters Patent is hereby corrected as shown below:

Column 8,
Line 48, "bars (///)" should be -- bars (\\\) --.

Column 13,
Line 62, "100µl" should be -- 100 µM --.

Column 18,
Line 52, "(Coming" should be -- (Corning --.

Column 19,
Line 56, "$^{32}$p" should be -- $^{32}$P --.

Column 21,
Line 66, "IU" should be -- HU --.

Signed and Sealed this

Seventeenth Day of June, 2003

JAMES E. ROGAN
*Director of the United States Patent and Trademark Office*